US012653920B2

(12) United States Patent
Bahremand et al.

(10) Patent No.: US 12,653,920 B2
(45) Date of Patent: Jun. 16, 2026

(54) SYSTEMS, METHODS, AND APPARATUSES FOR IMPLEMENTING OLFACTORY DELIVERY IN VIRTUALIZED ENVIRONMENTS USING AN OLFACTORY DELIVERY ENGINE

(71) Applicant: Arizona Board of Regents on Behalf of Arizona State University, Scottsdale, AZ (US)

(72) Inventors: Alireza Bahremand, Mesa, AZ (US); Richard Gerkin, Tempe, AZ (US); Mason Manetta, Mesa, AZ (US); Jessica Lai, Tempe, AZ (US); Robert LiKamWa, Tempe, AZ (US); Brian Smith, Phoenix, AZ (US); Christy Spackman, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 319 days.

(21) Appl. No.: 18/553,089

(22) PCT Filed: Apr. 1, 2022

(86) PCT No.: PCT/US2022/023152
§ 371 (c)(1),
(2) Date: Sep. 28, 2023

(87) PCT Pub. No.: WO2022/212906
PCT Pub. Date: Oct. 6, 2022

(65) Prior Publication Data
US 2024/0269336 A1 Aug. 15, 2024

Related U.S. Application Data

(60) Provisional application No. 63/169,635, filed on Apr. 1, 2021.

(51) Int. Cl.
*A61L 9/12* (2006.01)
*A61M 21/02* (2006.01)
(Continued)

(52) U.S. Cl.
CPC ............. *A61L 9/125* (2013.01); *A61M 21/02* (2013.01); *A63F 13/28* (2014.09); *G05D 11/13* (2013.01);
(Continued)

(58) Field of Classification Search
CPC ................. A61L 9/125; A61L 2209/11; A61L 2209/134; A63F 13/28; A61M 21/02;
(Continued)

(56) References Cited

U.S. PATENT DOCUMENTS 8,778,409 B2 * 7/2014 Vodyanoy ............. A61M 31/00
424/641
2016/0287161 A1 * 10/2016 Smith .................. A61B 5/4011
(Continued)

FOREIGN PATENT DOCUMENTS

JP 2007079620 A 3/2007
JP 5477740 B2 4/2014

OTHER PUBLICATIONS

Bahremand et al., "The Smell Engine: A system for artificial odor synthesis in virtual environments", IEEE Conference on Virtual Reality and 3D User Interfaces (VR), IEEE, Mar. 12, 2022, pp. 241-249.
(Continued)

*Primary Examiner* — Hussein Elchanti
(74) *Attorney, Agent, or Firm* — Shumaker & Sieffert, P.A.

(57) ABSTRACT

Exemplary implementations for olfactory delivery in virtualized environments using an olfactory delivery engine are described. Mimicking physical odor sensations virtually can
(Continued)

present users with a real-time odor synthesis that approximates what users would smell in a virtual environment, e.g., as they walk around in virtual reality. An exemplary Smell Engine includes: (i) a Smell Composer framework that allows developers to configure odor sources in virtual space, (ii) a Smell Mixer that dynamically estimates the odor mix that the user would smell, based on diffusion models and relative odor source distances, and (iii) a Smell Controller that coordinates an olfactometer to physically present an approximation of the odor mix to the user's mask from a set of odorants channeled through controllable flow valves. Experimental results show that the Smell Engine can help measure a subject's olfactory detection threshold and improve their ability to precisely localize odors in the virtual environment.

20 Claims, 17 Drawing Sheets

(51) Int. Cl.
*A63F 13/28* (2014.01)
*G05D 11/13* (2006.01)
*A61M 21/00* (2006.01)

(52) U.S. Cl.
CPC ...... *A61L 2209/11* (2013.01); *A61L 2209/134* (2013.01); *A61M 2021/0016* (2013.01); *A61M 2021/005* (2013.01)

(58) Field of Classification Search
CPC .... A61M 2021/0016; A61M 2021/005; G05D 11/13
See application file for complete search history.

(56) References Cited

U.S. PATENT DOCUMENTS

| | | | | |
|---|---|---|---|---|
| 2018/0071425 | A1* | 3/2018 | Jin | A61L 9/125 |
| 2019/0114671 | A1* | 4/2019 | Briggs | G06F 3/04815 |
| 2019/0176034 | A1* | 6/2019 | Flego | B05B 7/2416 |
| 2020/0191155 | A1* | 6/2020 | Firestein | F04D 25/16 |
| 2021/0209153 | A1* | 7/2021 | Zhang | G06F 3/013 |
| 2021/0217243 | A1* | 7/2021 | Shchur | G02B 27/0172 |
| 2021/0370189 | A1* | 12/2021 | Manuel | A63F 13/90 |
| 2022/0114653 | A1* | 4/2022 | Boghossian | G06Q 30/0643 |
| 2022/0180027 | A1* | 6/2022 | Hartmann | G06F 30/27 |
| 2022/0240779 | A1* | 8/2022 | Peyman | A61B 5/441 |
| 2022/0262504 | A1* | 8/2022 | Bratty | G16H 20/30 |
| 2022/0291328 | A1* | 9/2022 | Ozturk | G01S 5/0226 |

OTHER PUBLICATIONS

Harrison et al., "Engaging the five senses in space through Arizona State University's interplanetary initiative", 70th International Astronautical Congress, International Astronautical Federation, Oct. 21, 2019, 6 pp.
International Preliminary Report on Patentability from International Application No. PCT/US2022/023152 dated Oct. 3, 2023, 14 pp.
International Search Report and Written Opinion of International Application No. PCT/US2022/023152 dated Aug. 2, 2022, 15 pp.

* cited by examiner

Odorants
101

Solenoid Valves
(e.g., "valves")
102

Manifold Assembly
(to connect valves)
103

Mass Flow Controllers
(to Control Flow Rate)
104

Virtual Environments
105

Smell Mask
165

Smell Mask
165

$$y_i = f_A \frac{w_{iA}}{\sum\limits_{k=1}^{n} w_{kA}} + f_B \frac{w_{iB}}{\sum\limits_{k=1}^{n} w_{kB}}$$

Equation (1)

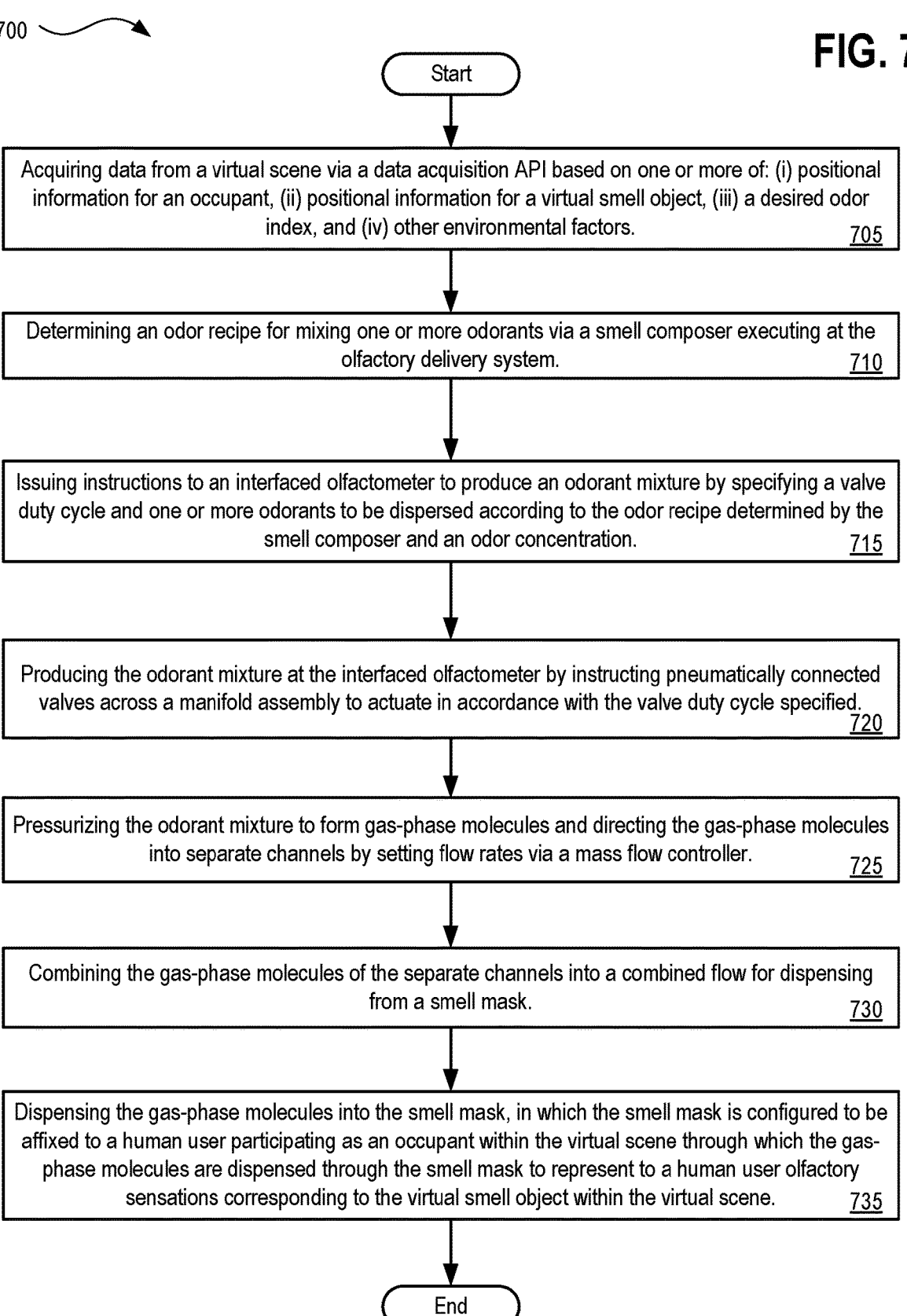

Start

Acquiring data from a virtual scene via a data acquisition API based on one or more of: (i) positional information for an occupant, (ii) positional information for a virtual smell object, (iii) a desired odor index, and (iv) other environmental factors.                                                705

Determining an odor recipe for mixing one or more odorants via a smell composer executing at the olfactory delivery system.                                                710

Issuing instructions to an interfaced olfactometer to produce an odorant mixture by specifying a valve duty cycle and one or more odorants to be dispersed according to the odor recipe determined by the smell composer and an odor concentration.                                                715

Producing the odorant mixture at the interfaced olfactometer by instructing pneumatically connected valves across a manifold assembly to actuate in accordance with the valve duty cycle specified.                                                720

Pressurizing the odorant mixture to form gas-phase molecules and directing the gas-phase molecules into separate channels by setting flow rates via a mass flow controller.                                                725

Combining the gas-phase molecules of the separate channels into a combined flow for dispensing from a smell mask.                                                730

Dispensing the gas-phase molecules into the smell mask, in which the smell mask is configured to be affixed to a human user participating as an occupant within the virtual scene through which the gas-phase molecules are dispensed through the smell mask to represent to a human user olfactory sensations corresponding to the virtual smell object within the virtual scene.                                                735

End

SYSTEMS, METHODS, AND APPARATUSES FOR IMPLEMENTING OLFACTORY DELIVERY IN VIRTUALIZED ENVIRONMENTS USING AN OLFACTORY DELIVERY ENGINE

GOVERNMENT RIGHTS AND GOVERNMENT AGENCY SUPPORT NOTICE

This invention was made with government support under ROI DC018455 awarded by the National Institutes of Health. The government has certain rights in the invention.

CLAIM OF PRIORITY

This patent application, filed under the Patent Cooperation Treaty (PCT), is related to and claims priority to the U.S. Provisional Application No. 63/169,635 entitled "SYSTEMS, METHODS, AND APPARATUSES FOR IMPLEMENTING AN AUGMENTED REALITY OLFACTORY DELIVERY ENGINE," filed Apr. 1, 2021, the entire contents of which are incorporated herein by reference as though set forth in frill.

COPYRIGHT NOTICE

TECHNICAL FIELD

Embodiments of the invention relate generally to the field of augmented reality gaming devices, and more particularly, to systems, methods, and apparatuses for implementing olfactory delivery in virtualized environments using an olfactory delivery engine.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Incorporating smell into immersive virtual environments would revolutionize current uses and allow expansion into new applications such as healthcare, training for extreme environments, multi-sensory entertainment experiences, and archival efforts in a rapidly changing world.

Problematically, existing olfactory display systems operate as standalone systems that generate limited odors through gas mixtures with limited contextualization of digital or physical spaces. Attempts by these devices to synthesize smells to mimic a real odor have been crude due to a limited number of ingredients, incorrect relative concentrations of odorants, and unrefined composition of odor profiles. As a result, current virtual and augmented reality experiences fail to fully engage the senses, specifically the sense of smell, in a more integrated multi-modal fashion.

What is needed is an olfactory delivery system that is analogous to visual/auditory rendering engines, linking programmable software integration with olfactory display systems that compose, deliver, and sense odors in real-time in response to user behavior.

The present state of the art may therefore benefit from the systems, methods, and apparatuses for implementing olfactory delivery in virtualized environments using an olfactory delivery engine, as is described herein.

BRIEF DESCRIPTION OF THE DRAWINGS

Embodiments are illustrated by way of example, and not by way of limitation, and can be more fully understood with reference to the following detailed description when considered in connection with the figures in which;

FIG. 3D depicts presents equation (1) for use with described embodiments;

FIG. 7 depicts flow diagrams illustrating a method for implementing olfactory delivery in virtualized environments using an olfactory delivery engine, in accordance with described embodiments.

DETAILED DESCRIPTION

Figure 1A:
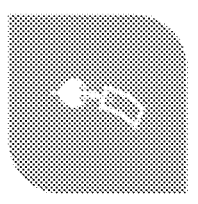
FIG. 1A depicts an exemplary system block diagram 100 of the augmented reality olfactory delivery engine, in accordance with described embodiments.
Figure 1A:
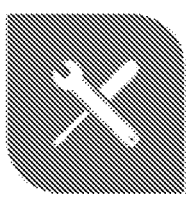
Figure 1A:
Figure 1A:
Figure 1A:
Figure 1A:
Figure 1A:
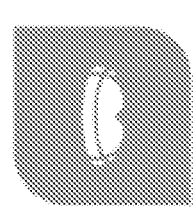

Described herein are systems, methods, and apparatuses for implementing olfactory delivery in virtualized environments using an olfactory delivery engine. For instance, there is a method performed by an augmented reality olfactory delivery engine (also referred to herein as a "smell engine") having at least a processor and a memory communicably interfaced with odorant control hardware, in which the method includes the following operations: acquiring data from a virtual scene via a data acquisition API based on one or more of: (i) positional information for an occupant, (ii) positional information for a virtual smell object, (iii) a desired odor index, and (iv) other environmental factors; determining an odor recipe for mixing one or more odorants via a smell composer executing at the olfactory delivery system; issuing instructions to an interfaced olfactometer to produce an odorant mixture by specifying a valve duty cycle and one or more odorants to be dispersed according to the odor recipe determined by the smell composer and an odor concentration; producing the odorant mixture at the interfaced olfactometer by instructing pneumatically connected valves across a manifold assembly to actuate in accordance with the valve duty cycle specified; pressurizing the odorant mixture to form gas-phase molecules; directing the gas-phase molecules into separate channels by setting flow rates via a mass flow controller; combining the gas-phase molecules of the separate channels into a combined flow for dispensing from a smell mask; and dispensing the gas-phase molecules into the smell mask, wherein the smell mask is configured to be affixed to a human user participating as an occupant within the virtual scene through which the gas-phase molecules are dispensed through the smell mask to represent to a human user olfactory sensations corresponding to the virtual smell object within the virtual scene.

As humans, our sense of smell—also known as olfaction—allows us to navigate rich environments of scents that signal appetite, threat, nostalgia, and other feelings. Through mental association with previous experiences, olfaction allows us to prepare for the situation at hand. Infused alongside visual, auditory, and tactile cues, the spatial and temporal nature of odor allows humans to associate scents with specific objects and areas, thereby informing how to interpret and handle various situations, especially when navigating unfamiliar environments or events. Allowing virtual environments to similarly produce odors produce spatiotemporal olfactory cues would provide a platform for multi-sensory training, education, memory, and several other use cases. This is important for virtual reality and augmented reality, as immersive visual and auditory systems would be expanded with olfactory systems to accompany them.

Thus, there exists a compelling opportunity to advance the arts by synthesizing physical odors which mimic what a user would experience while exploring an odor-infused virtual environment with virtual objects. Prior techniques are limited to producing specific pre-mixed odor mixes and perfumes, which are specifically triggered via virtual cues. Conversely, described herein is a virtual olfaction system that is more naturally integrated into spatio-temporal virtual environments among other multi-sensory stimuli.

More specifically, a software framework is presented that is:

1. Spatiotemporally reactive: responsive to a user's position in relation to the odors and events in the virtual environment, the framework modifies the mix and strength of the odors as they arrive at the user's virtual nose;
2. Expressive in scent programmability: The framework offers developers and designers the ability to program a wide range of odor profiles, odor intensities, and odor dispersion characteristics into the virtual environment;
3. Modular in operation: The framework provides hardware abstraction layers to control odor-synthesizing hardware and platform interfaces to explore further modes of odor-mixing hardware; and
4. Multi-sensory integration: The framework may be embedded within a standard game engine design/development for integration alongside visual and auditory sensations.

The Smell Engine, as described herein, may include by way of example: (i) a Smell Composer framework that allows developers to configure odor sources in virtual space, (ii) a Smell Mixer that dynamically estimates the odor mix that the user would smell, based on diffusion models and relative odor source distances, and (iii) a Smell Controller that coordinates a hardware olfactometer to physically present an approximation of the odor mix to the user's mask from a set of odorants channeled through controllable flow valves. According to one exemplary embodiment, the Smell Engine was integrated with the Unity Game Engine, allowing designers to place odors and specify their dispersion characteristics at design time, and stimulating distance based odor mixing at runtime, produced through the hardware valve system. The described Smell Engine framework operates alongside existing visual and auditory systems of the Unity Game Engine, using the position of the user's virtual camera as a rough estimation of the position of the user's virtual "nose." Altogether, the described solution and implementation provides an end-to-end system for artificial odor synthesis of virtual environments.

Commands issued by the smell engine may control the duty cycles for each of an arbitrary number of solenoid valves in a pneumatic manifold and the set-points of each of several mass flow controllers, which may be fewer than the number of valves available and operate to produce a desired odorant mixture.

Embodiments described herein operate in conjunction with a smell mask which is specially adapted to be worn by a human user participating within a virtual scene or virtual environment (e.g., within virtual reality or within an augmented reality environment known as "VR" or "AR" respectively).

The dispensed gas-phase molecules represent the virtual smell object encountered by a human user participating within the VR/AR scene and the dispensed gas-phase molecules then simulate to the human user (assuming the user is wearing the smell mask), a desired olfactory sensation the wearer.

Further processing operations which may be performed include computing, via a sequence of linear and non-linear optimization techniques continuously running, the desired concentration(s) and flow rate(s) which are then updated in real time. As used herein, the system hardware parameters observes, monitors, senses, or determines these desired values in proximity to the nose of the human user (again, assuming the human user is wearing the mask).

According to a particular embodiment, there is an odor delivery system which further includes functionality to continuously update hardware parameters of connected odor delivery control components, including continuously updating the valve states of valve controllers, continuously updating the flow controller set points of flow controllers, etc., so as to achieve an arbitrary target odor as defined by controlling software rendering the virtual scene. This is in contrast to prior known techniques which rely upon event-driven triggers, such as triggering an event specifically upon some pre-determined moment in time or upon an object or participant arriving upon some pre-determined position in virtual space, or when a pre-determined device pattern is activated and sensed by the control software.

The ability to continuously update and continuously specify control parameters and set points in time and (virtual) space as is described herein therefore greatly improves upon prior known technologies. According to a particular embodiment, this is achieved via a sequence of optimization steps (a least-squares linear optimization followed by a non-linear optimization) that map the desired odor parameters to these hardware states. For instance, such optimization steps may be run continuously (such as iteratively every few tens of milliseconds). According to such embodiments, output from the vessels containing the odors is multiplexed via the interfaced valves through a number of mass flow controllers which is fewer than the number of vessels.

Such an approach is novel and advantageous over prior known techniques as such prior methodologies would require, for example, N=# of vessels or N=1. Conversely, methodologies described herein dynamically route odorants from their vessels to whatever mass flow controller or to a combination of mass flow controllers, which thus enables the target odor (e.g., the desired concentration(s) and flow rates(s)) at the nose of the participant (e.g., such as a human user within the virtual scene) to be achieved and thus sensed by the user. In such a way, use of the N<# of vessels achieves significant cost savings as the mass flow controllers are the most expensive hardware component.

Still further, described methodologies attain a much higher and unprecedented dynamic range in odor concentration from fixed in-vessel dilutions by using mass flow controllers with distinct and complementary operating ranges, e.g. one that works between 0.01-10 mL/min of flow, and one that works between 10-10000 mL/min of flow. This technique thus overcomes limitations in the dynamic range of solenoid or proportional valves as was present in prior known techniques.

Notably, the technology creates and dispenses odors to enhance virtual reality visual and auditory experiences. The technology integrates software programmable olfactory display systems with existing 3D game engine software. The described augmented reality olfactory delivery engine dynamically maps user exploration in a virtual world to olfactory sensations via programmed actuation of the output channels from the olfactory display device. In such a way, when a user moves around a virtual scene, the device mixes and emits odors in real-time to enhance the user's experience pursuant to instructions given to the device by the augmented reality olfactory delivery engine. In addition to enhancing virtual reality gaming, the smell engine may also be used in battlefield and other training simulations, educational applications, and medical applications such as therapies for those who have experienced a stroke, brain injury or suffer from a neurodegenerative disease. The smell engine is an improvement on existing stand-alone olfactory display systems that are crude with a limited number of odors and operate with limited contextualization of digital or physical spaces.

Key features include (1) the capability for integrating 3D game engine software with an odor mixing and dispensing device, (2) configurable computer programmable mixing and dispensing of the odor producing chemicals is done in real-time in response to a user navigating a virtual environment, (3) dispensing of odor and, in addition to the actual odor, configurable control of odor strength via the programmable computing interface in-situ, such that both the odor and the odor strength are dynamically manipulated in real-time based upon the user's movement toward and away from an odor producing object (e.g., a virtually rendered object which should be perceived by the user as the source of the odor) within in the virtual environment, (4) utilizing within realistic virtual reality games, simulators and educational applications as well as the increased immersion and the users perception of the virtual reality as being more realistic than is possible with prior known techniques, and (5) configurable use of the technology for medical applications such as rehabilitation for stroke victims and people who suffer from neurodegenerative diseases.

In the following description, numerous specific details are set forth such as examples of specific systems, languages, components, etc., in order to provide a thorough understanding of the various embodiments. It will be apparent, however, to one skilled in the art that these specific details need not be employed to practice the embodiments disclosed herein. In other instances, well known materials or methods have not been described in detail in order to avoid unnecessarily obscuring the disclosed embodiments.

In addition to various hardware components depicted in the figures and described herein, embodiments further include various operations which are described below. The operations described in accordance with such embodiments may be performed by hardware components or may be embodied in machine-executable instructions, which may be used to cause a specialized and special-purpose processor having been programmed with the instructions to perform the operations described herein. Alternatively, the operations may be performed by a combination of hardware and software. In such a way, the embodiments of the invention provide a technical solution to a technical problem.

Embodiments also relate to an apparatus for performing the operations disclosed herein. This apparatus may be specially constructed for the required purposes, or it may be a special purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various customizable and special purpose systems may be used with programs in accordance with the teachings herein, or it may prove convenient to construct more specialized apparatus to perform the required method steps. The required structure for a variety of these systems will appear as set forth in the description below. In addition, embodiments are not described with reference to any particular programming language. It will be appreciated that a variety of programming languages may be used to implement the teachings of the embodiments as described herein.

Embodiments may be provided as a computer program product, or software, that may include a machine-readable medium having stored thereon instructions, which may be used to program a computer system (or other electronic devices) to perform a process according to the disclosed embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical), etc.

Any of the disclosed embodiments may be used alone or together with one another in any combination. Although various embodiments may have been partially motivated by deficiencies with conventional techniques and approaches, some of which are described or alluded to within the specification, the embodiments need not necessarily address or solve any of these deficiencies, but rather, may address only some of the deficiencies, address none of the deficiencies, or be directed toward different deficiencies and problems which are not directly discussed.

In addition to various hardware components depicted in the figures and described herein, embodiments further include various operations which are described below. The operations described in accordance with such embodiments may be performed by hardware components or may be embodied in machine-executable instructions, which may be used to cause a special-purpose processor programmed with the instructions to perform the operations. Alternatively, the operations may be performed by a combination of hardware and software, including software instructions that perform the operations described herein via memory and one or more processors of a computing platform.

FIG. 1A depicts an exemplary system block diagram 100 of the augmented reality olfactory delivery engine, in accordance with described embodiments.

Figure 1B:
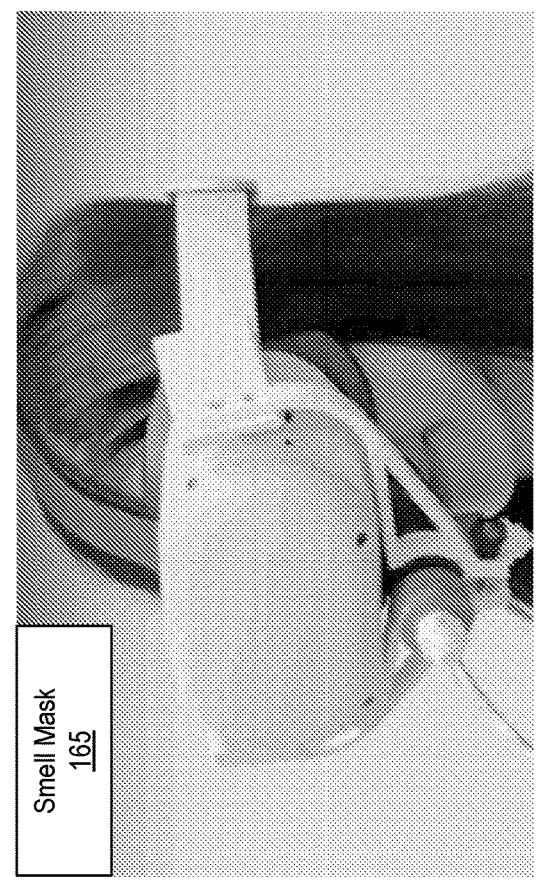
FIG. 1B depicts an exemplary smell mask 165 in the form of a human wearable apparatus when used in conjunction with the described embodiments.
Figure 1B:
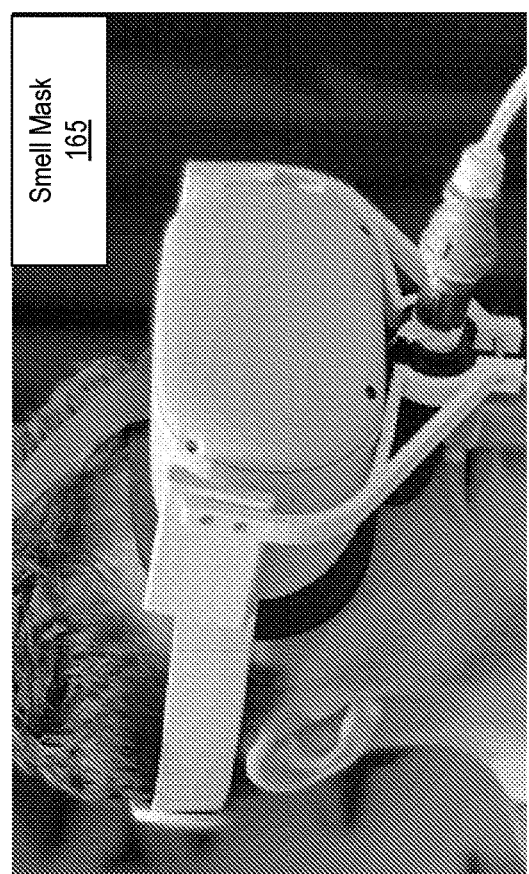

FIG. 1B depicts an exemplary smell mask 165 in the form of a human wearable apparatus when used in conjunction with the described embodiments.

As shown here, stored odorants 101, which according to certain embodiments may be liquid, oil, extract, semi-solid, or solid materials, and further may be stored in compartments or capsules, are mixed via solenoid valves 102 when a desired odor needs to be emitted in an augmented reality or virtual reality environment, for example in association with a virtual smell object. A manifold assembly to connect valves 103 allows control of mixing and pressurizing odorants to the gas-phase. To temporally control which odorants and the amounts of odorants are delivered to specified mass flow controllers, one solenoid valve 102 is used for each odorant. Covered by a hood, the valves 102 are connected by a programmable manifold assembly 103 that pneumatically connects different ports together.

The intensity and range of a desired odor may be controlled via mass flow controllers to control flow rate 104. Modulating flow rates may be necessary to vary the intensity and dispersion of a desired odor, for example, based on dynamic positioning of occupants in virtual environments 105 that wear, for example, a smell mask that delivers the desired odor.

Virtual and augmented reality experiences provide users with complex visual, auditory, and haptic or tactile inputs for gaming or to assist in a variety of training exercises. However, current systems only partially integrate smell, a critical component of the sensory experience, into virtual environments. This means that one of the core human modes of navigating the world, the sense of smell, remains incompletely engaged in gaming and training simulations using virtual and augmented reality. This leaves users unprepared for the entire sensory landscapes that they may be training for, such as acclimating to the smell of elevated sulfur concentrations on planets such as Mars.

Incorporating smell into immersive virtual environments would revolutionize current uses and allow expansion into new applications such as health screening, future casting (scenario planning using emerging technologies), multisensory entertainment experiences, and archival efforts in a rapidly changing world. To accomplish this, a "smell engine" or olfactory delivery system is needed that is analogous to visual/auditory rendering engines, linking programmable software integration with olfactory display systems that compose, deliver, and sense odors. This programmable olfactory delivery engine integrates olfactory display systems with existing 3D game engine software to accurately compose and modify smells in real-time in response to user behavior. According to certain embodiments, integration involves the creation of an olfactory grid that operates in equivalence to visual and auditory sensations, and is fully integrated with, and makes use of, the spatial capabilities of virtual game engines.

Existing olfactory display systems operate as standalone systems that generate limited odors through gas mixtures. These devices employ micropumps, piezo sensors, microfans, and gas modules. Additionally, they operate with limited contextualization of digital or physical spaces. Attempts by these devices to synthesize smells to mimic a real odor have been crude, due to a limited number of ingredients, incorrect relative concentrations of odorants, and the lack of a validated statistical model to guide the composition of odor profiles. As a result, current virtual and augmented reality experiences fail to fully engage user senses, specifically the sense of smell, in a more integrated multi-modal fashion.

The present olfactory delivery engine is programmable and integrates olfactory display systems with existing 3D game engine software to accurately compose and modify smells in real-time in response to user behavior. Benefits also include adaptability and portability with virtual reality and augmented reality desktop and mobile hardware.

The olfactory delivery engine will dynamically map user exploration of a virtual scene to olfactory sensations via programmed actuation of the output channels from olfactory display devices, represented in the virtual scene as a virtual smell object. This can be achieved by providing: i) parameterized attributes for any molecular odorants such as diffusion constants and molecular concentrations, ii) spatiotemporally pressurized odor delivery capabilities, iii) versatility in controlling, blending, and synthesizing multiple scents simultaneously, and iv) adaptability in hardware design/specification.

The olfactory delivery engine integrates olfactory display devices with user exploration in virtual environments through precise programmed actuation of olfactory display channels. The smell engine links programmable software integration with olfactory display devices to accurately compose and modify smells in real-time in response to user behavior. As a user navigates a virtual environment of programmable scents, the system will adapt the presented odor to match the concentration of constituent odorants through real-time mixing. The olfactory delivery engine solves several research challenges, including:

(i) Expressiveness: accurately represents any odor profiles and dispersion in spatial environments.

(ii) Modularity/extensibility: giving developers flexible control to adjust olfaction-related settings to meet use case needs.

(iii) Multi-sensory integration: integrating with the spatial visual and auditory capabilities of virtual game engines.

Thus, the olfactory delivery engine can be conceptualized as a pipeline for generating, processing, and synthesizing odor samples in synchrony with 3D game engine runtimes.

Optimization Module.

The olfactory delivery engine is a framework for orchestrating and synthesizing odor recipes using an optimization module to fine-tune various parameters including: (i) closely matching desired odors using similar odor recipes with different connected odorants, (ii) determining best airflow rates and valve duty cycles to pressurize liquid odorants to gas-phase molecules, (iii) determining components that can be ignored or clipped to meet human sensory needs, (iv) specifying varied odor strengths for artificial synthesis, integrating software in real-time with 3D game engines, (v) providing a programmable environment for developers to specify virtual odor position(s) in virtual environments/spaces. (vi) adapting odor composition according to virtual distance-based on-the-fly dynamics, and (vii) making optimization decision regarding which odorants are capable of making mixtures at different ratios and concentrations. According to certain embodiments, there is a programmable interface for testing and generating odor recipes using any olfactory display hardware configuration. A real-time communication framework allows for calculating and transmitting desired odorant concentrations between virtual environments and olfactory display systems. A virtual interface allows for actuating hardware valves and control gas-phase concentrations of odorants dynamically in response to a virtual context.

The olfactory delivery engine is composed of various components including hardware olfactory display, multiplex odorants delivered through flow controllers, a system for on-the-fly delivery, and a manifold design that uses fewer than one mass flow controller (MFC) per odorant. There is also a software interface for system designers to virtually define, configure, test, and represent the physical components of their system in real-time, ranging from the number of solenoid valves and MFCs, to the liquid volume of each molecular odorant.

Implementation Details.

The olfactory delivery engine controls olfactometer valve states and MFC flow rates in parallel by utilizing open-source computer programs and hardware components created by National Instruments (NI). These data acquisition (DAQ) programs and system components provide us with 96-channels of A/D communication and multifunction I/O modules. The olfactory delivery engine is developed with NF's application programming interface (API), NIDAQmx, to enable software control of the hardware's I/O.

Generally speaking, an olfactometer is an instrument used to detect and measure odor dilution. Olfactometers are used in conjunction with human subjects in laboratory settings, market research, and entertainment. Olfactometers are used to gauge the odor detection threshold of substances and to measure, for example, intensity of a subject odorous gas against a known baseline gas.

The olfactometers utilized in accordance with the described embodiments are specially configured to present odor stimuli in a standardized computer-controlled manner with determined air flow, odor concentration, odor duration, onset, and offset. The generated and presented odor may be utilized in conjunction with, for example, delivery and enhancement of educational materials in an academic setting, entertainment content, as well as in the context of research conducted with human subjects. In addition to the generation and presentment of odorous gasses from the olfactometers described herein, certain embodiments additionally control non-odor environmental factors which are delivered to a human subject, including the control of humidity, temperature, and intensity of flow. Other features can be also be configured and controlled.

In order to verify efficient usage of the API, hardware components were modeled into object-oriented classes and a software simulation of hardware functionality was developed to perform a suite of system unit tests. Such unit tests allow for the verification of system metrics such as odorant depletion rates, timely execution of hardware actuation, active states of odorant valves, the period of diffusion rates per odorant, and error rates of desired versus generated odorant concentrations, all in real-time.

Users can define any odor recipe for simultaneous mixing in response to user exploration, according to protocols for programmable configuration and representation of olfaction data. Programmability of odors includes defining individual odorants and specifying concentrations. Flow rates affecting the rate of odor diffusion are also programmable.

Real-time software provides a representation of hardware components of the olfactory delivery engine to a fine level of granularity, including, for example, the depletion of liquid odorants. Software support is also provided for the synthesis of various odorant substances, i.e., liquids and essential oils.

A common shortcoming of olfactory display technology revolves around a limited selection of arbitrary scents, one-off application examples, and varied system designs. The current state-of-the-art relies on essential oils or pre-delivered cartridges that provide a fixed number of options at discrete intervals and concentrations, much like ink cartridges for computer printers. Thus, the olfactory delivery engine is an improvement on existing stand-alone olfactory display systems that are crude with a limited number of odors and operate with limited contextualization of digital or physical spaces.

According to certain embodiments of the olfactory delivery engine, odor strength changes along a continuous path and is responsive to user position/navigation in virtual spaces. There is also a high dynamic range with six orders of magnitude. These features decrease the cost of prototyping user experience in high-risk or high-cost product development by conserving the amounts of odorants prepared and dispensed, such as in the development of cosmetic fragrances including perfumes and colognes, or developing aromas to enhance food products.

Furthermore, the olfactory delivery engine provides users with a pipeline to capture odors via odor recording technologies and then rendering those odors using olfactory display technologies.

The olfactory delivery engine dynamically maps user exploration in a virtual world to olfactory sensations via programmed actuation of output channels from the olfactory display device. Thus, computer programmable mixing and dispensing of odor-producing chemicals is done in real-time in response to a user-occupant navigating a virtual environment. For example, when a user-occupant moves around a virtual scene, the device mixes and emits odors in real-time to enhance the user's experience. In addition to the actual odor, odor strength is also controlled during the user's movement towards and away from an odor-producing object in the virtual environment, via the adjustment of odorant concentrations and flow rates.

Beyond enhancing virtual reality gaming, the olfactory delivery engine may also be used in battlefield and other training simulations, educational programs, and healthcare, such as diagnosis, rehabilitation and therapy for those who have experienced a stroke, brain injury, or suffer from a neurodegenerative disease. Rest and relaxation-related services such as massage and aromatherapy may use the olfactory delivery engine in combination with virtual environments to add imagery, sounds, and scents to the ambiance within which services are performed.

The smell engine was evaluated experimentally through measurement-based studies and user studies. These studies measured the system's odor generation precision by using a Photo-Ionization Detector (PID) to measure outflowing gas concentration. It was observed that the Smell Engine can produce granular changes in odor strength in scales ranging from 10.0 picomolar to 1.0 millimolar. The user studies further evaluated the system's timeliness of odor delivery, the system's ability to help identify a user's olfactory detection thresholds, and the system's ability to help improve user localization of odor sources in a virtual environment.

The study additionally measured user-perceived latency. It was found that some users perceived odors relatively quickly, within 2.5 seconds, while others perceived odors more slowly, e.g., around 10 seconds. In a second user study, the Smell Engine was used to identify user perceivable "Just-Noticeable-Difference" (IND) thresholds for changes in olfactory stimulus magnitude. Not only could the Smell Engine help identify a subject's odor acuity levels, but it could generate odor concentrations at an even finer granularity than user-perceivable detection thresholds. A final user study investigated how accurately users can localize an odor source between the described approach for odor delivery compared with traditional collider-based delivery methods. The results show that the described odor delivery method improved the average user accuracy of the group by 43% and improved the average proximity of their odor source localization by 55%.

Thus, the described software-hardware framework integrates olfactory stimuli into virtual environments, such that odor strengths spatiotemporally vary based on user navigation and interaction, presenting odors through a mask-based apparatus.

Olfactory Displays (Wearable and Desktop): Olfactory display systems deliver olfactory stimuli through a variety of approaches, including Surface Acoustic Wave (SAW) devices, Piezoelectric sensors, ink-jet printers, and multi-component devices. An exemplary desktop olfactory display system directs odorous airflow to physically collide and spatially disperse odorant molecules (OM) at the user's nose. Simplified inexpensive systems can also direct odorant airflow to a user by vaporizing a liquid odorant using a fan, microcontroller, and 3D printed enclosure. Similarly, the available OSpace system presents scent delivery with parametric adjustments in timing, relative intensity of constituent odorants, flow rates, and air extraction.

Other wearable olfactory display research has investigated form factors including eyeglasses, necklaces, and VR HMD clamps, shortening the length/travel-time when delivering scents to the user's nose. In commercial realms, systems such as OVR Technologies, provide a wearable olfactory display that attaches to VR HMDs, comprising swappable odor vials, a custom Unity API to assign scent parameters to objects, and a fan to clear out millisecond-long bursts of scented liquids. Although such a system generates odors with different intensities, it is coarsely triggered by a collider and is therefore reliant upon pre-mixed scent profiles rather than leveraging the chemical or physical properties of the odorants themselves.

Virtually Parameterizing Olfactory Stimuli: To date, two approaches primarily account for how odor concentration varies spatially and temporally for a virtual environment. Specifically, user-navigable collider-based systems and Computational Fluid Dynamics (CFD) based systems which calculate the airflow field and how an odor disperses. Such systems demonstrate a tradeoff between computation time, wearability/portability, and accuracy of odor field virtualization.

Research exploring the odor mixing capabilities of olfactory displays has found that a modular system consisting of a micro-pump, liquid odorants connected to solenoid valves, and a SAW atomizer, can blend odors that are identical to pre-blended odors in liquid phase. To scale up the quantity of odorants and perceivable strength, a 24-scent multi-sensory display implementation capable of harnessing scent type, scent intensity, wind speed, and air temperature has been contemplated.

In favor of wearability and reduced computation time, implementations include a wearable olfactory display that atomizes a liquid odorant when the user virtually triggers a collider in the virtual environment. Other implementations include a wearable olfactory that modulated piezo-electric sensors to vaporize a set of liquid odorants towards the user's nose upon virtual collision with an odor-trigger object. Unfortunately, such systems are confined to a limited set of achievable odor selections and strengths. Greater control and variability of achievable odor selections is needed.

Certain implementations simulate a laminar-air flow model of user-perceived strength of an odor field by tuning parametric adjustments of delivery timing to explore greater accuracy in odor virtualization. Further improving accuracy in representing a virtual odor field, CFD simulations model how odorant concentrations evolve in both space and time. A CFD solver generates a matrix-like lookup table for instant lookup of odor concentration strengths based on the airflow and dispersal of a particular odorant at a distinct location, e.g., user's location at any given point in time. Although such a system presents smells more accurately, it suffers from computationally infeasible calculation times due to the requirement for pre-calculation—iterating over every object and its position in virtual space—ultimately resulting in a fixed, static representation of the virtual odor space.

Multisensory VR Systems: Other studies have focused on multi-sensory system design, sensory substitution, and stereo-olfactory displays, each studying the impact and challenges of integrating and creating multi-sensory stimuli for VR experiences. Certain implementations added olfactory and tactile (thermal and wind) stimuli to audio-visual stimuli and found that users felt increased immersion with multiple perceptual stimuli; however, users were not able to strictly attribute presence and immersion to olfactory stimuli potentially because of what is known as the "fundamental attribution error."

Solutions described herein raise the question of how critical it is that olfactory stimuli in virtual environments precisely replicate olfactory stimuli in real life for users to perceive the stimuli as "real." Novel research directions become available if stimuli experienced in virtual worlds can be mixed and used to reflect other stimuli sensations. For example, a device that tricks users into perceiving thermal sensations by stimulating the users' trigeminal nerve, may provide a better understanding of the relationships between thermal and olfactory stimuli.

To provide a sense of directionality for artificial olfaction, certain studies have explored stereo rendering of olfaction using chemical and electrical stimulation. For instance, a VR headset as equipped with a system that allows for switching between scents, altering the temperature of the air carrying the scents, changing the burst frequency of the scents, and specifying the directional airflow of the scents to the user using tubes clamped to the sides of the headset.

Described embodiments overcome the above noted shortcomings and improve upon prior designs through the use of a Smell Composer framework which allows developers to configure odor sources in virtual space, as described in greater detail below.

Figure 2A:
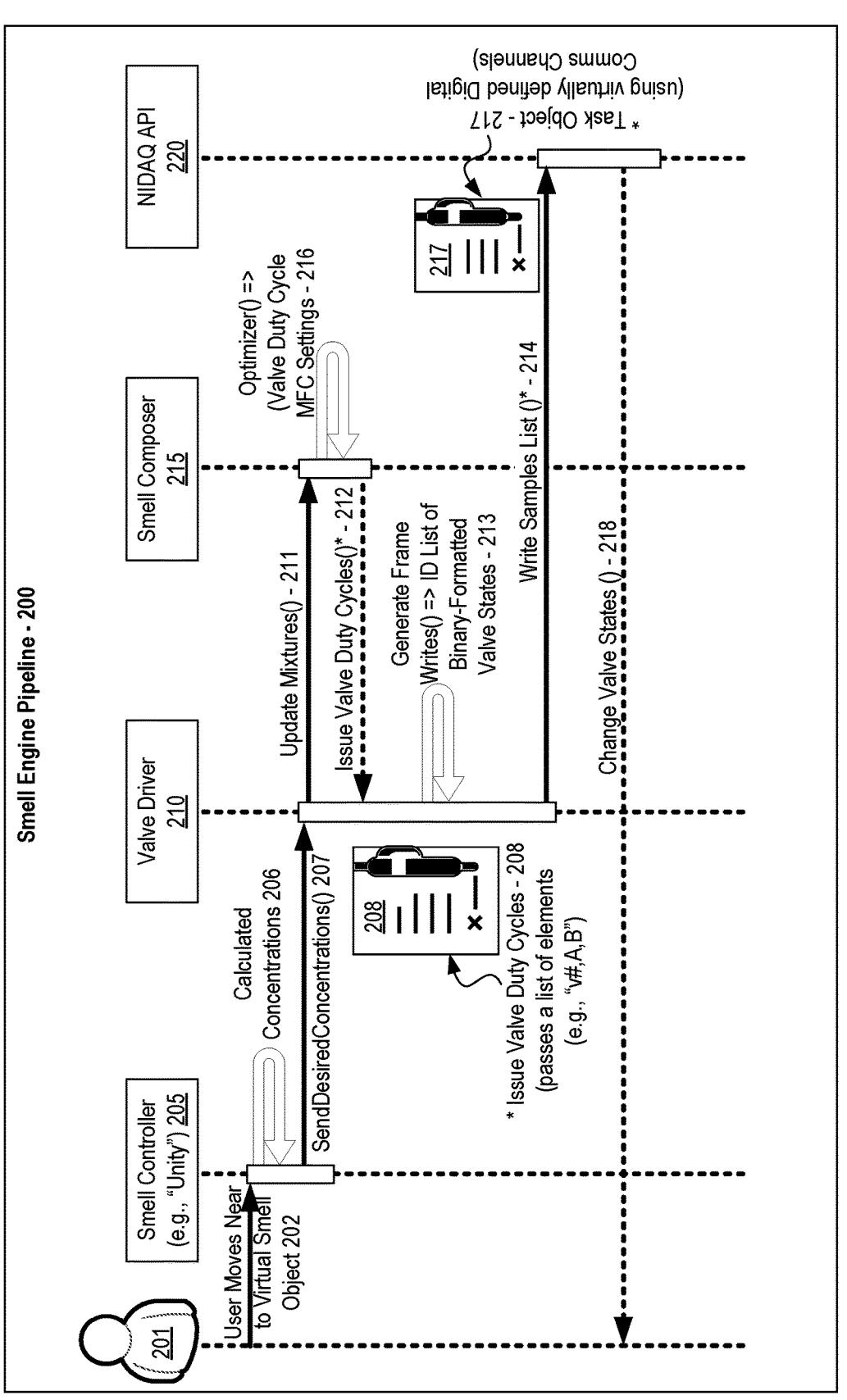
FIG. 2A depicts an exemplary smell engine pipeline flow diagram 200 of desired odorant production operations performed by the augmented reality olfactory delivery engine, in accordance with described embodiments.

FIG. 2A depicts an exemplary smell engine pipeline flow diagram 200 of desired odorant production operations performed by the augmented reality olfactory delivery engine, in accordance with described embodiments.

Figure 2B:
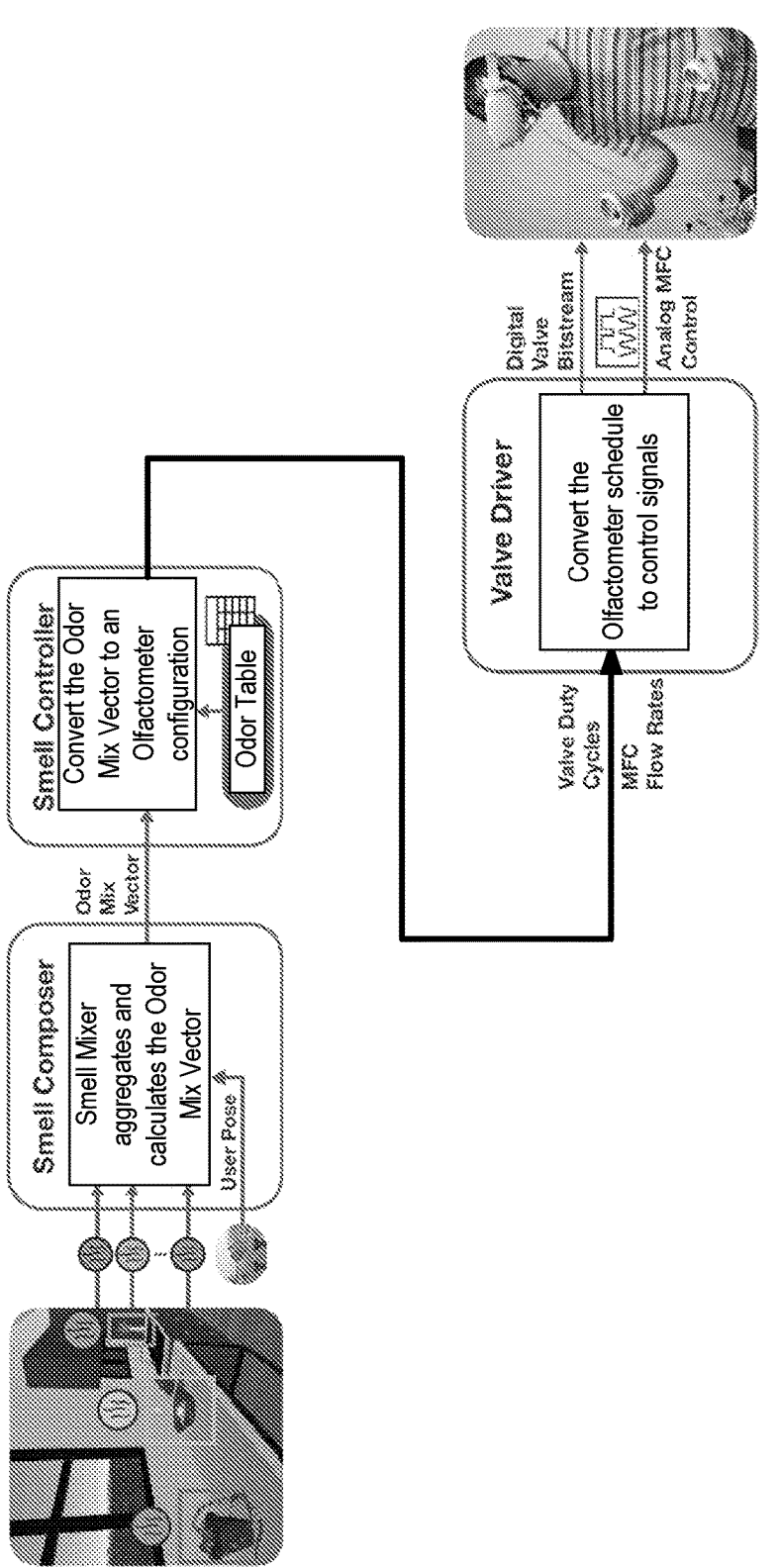
FIG. 2B depicts an exemplary a Smell Engine consisting of a Smell Composer, Smell Controller, and Valve Driver, in accordance with described embodiments.

FIG. 2B depicts an exemplary a Smell Engine consisting of a Smell Composer, Smell Controller, and Valve Driver, in accordance with described embodiments.

As depicted herein, the smell engine pipeline 200 consists of a Smell Composer 215, Smell Controller 205, and Valve Driver 210. Using the Smell Composer interface, designers create Odor Sources, which the Smell Mixer uses to calculate an Odor Mix Vector. The Odor Mix Vector is fed into the Smell Controller 205 to determine an olfactometer hardware configuration. This configuration is then fed into the Valve Driver 210 which actuates an olfactometer to generate the desired olfactory stimuli for the VR user.

As is further depicted, when user-occupant 201 in a virtual environment moves near virtual smell object 202, odors may be presented to the user 201. The augmented reality (AR) development framework "Unity" 205 is triggered to oversee the production of a desired odorant mixture. As part of initial operations, various functions are instantiated, including: CalculateConcentrations 206 which performs a calculation function, for example, of a concentration of the desired odor. Next, the function SendDesiredConcentrations 207 is instantiated to send the calculated concentration of the desired odor to valve driver 210 to next execute the UpdateMixtures 211 function at smell composer 215. Smell composer 215 may then issue a call to the Optimizer 216 function to determine valve duty cycles, MFC settings, and other parameters. Smell composer 215 then executes the IssuevalveDutyCycles 212 function which instruct valve driver 212 on valve operations of producing desired odorant mixtures including passing a list 208 of elements such as valve numbers and names to set valve duty cycles.

As used herein, the valve duty cycles may be understood as defining or specifying the ratio of time open versus the ratio of time closed for an automated actuator capable of receiving instructions or commands to operate (e.g., open and close) from some control module, such as the smell composer 215 which executes the IssuevalveDutyCycles 212 function to activate and initiate a controlled release of odorants.

A duty cycle of 100% would mean that the valve in question is actuated (e.g., opened) for its entirety of a controlled cycle or period of operational time. Conversely, a duty cycle of 50% means that for the period in question, the valve is open only half the time or only half way, depending on the configuration and specific release instructions issued by the smell composer 215. A typical duty cycle in the context of valve automation is defined as the ratio of actuation on time (e.g., valve open) to off time (e.g., valve closed which is the default state). The duty cycle may also be used select a properly configured actuator for a specific application. Correct specification of the valve duty cycle is necessary in order to determine acceptable operating times and to stay within proper operational limits to avoid the possibility of thermal over load to the actuator motor, especially in the context of an automated determination and valve duty cycle operational environment.

Valve driver 210 may also execute the GenerateFrameWrites 213 function which produces a ID list of binary-formatted (on/off) valve states. Valve driver 210 may also call the WritesamplesList 214 function to the National Instruments Data Acquisition API (NIDAQ API) 220. According to certain embodiments the function WriteSamplesList 214 may be called to execute via a task object using virtually defined digital communication channels 217.

Finally, NIDAQ API 220 may execute the Changevalvestates 218 function in coordination with, for example, smell composer 215, valve driver 210, and AR development framework Unity 205. The function Changevalvestates 218 may start, modify, or halt the production of desired odor mixtures for eventual emission into the virtual environment, for example via a smell mask worn by user-occupant 201. This may be done, for example, based on changing factors in the relevant virtual environment, such as user-occupant's 201 position relative to a virtual smell object.

Odor Science

Odor Mix Vector: Human perception of smell comes from specialized olfactory sensory neurons. Microscopic odorous molecules $(OM)^2$ bind to and activate specialized receptors on these neurons, which send messages to the human brain, which in turn decodes the activation of specific combinations of olfactory neurons into distinct smells. Most real odor mixtures—as experienced in nature—comprise different OMs at varying concentrations. Increasing the concentration of a single OM influences its perceived olfactory intensity, i.e. how strong it smells. Changing the relative concentration of OMs in a mixture can change the olfactory character of the stimulus, i.e., what is smells like.

For an odor to be detectable by a human, the concentration of at least one OM must exceed a detection threshold; for a change in concentration to be detected, the absolute change must exceed the so-called Just-Noticeable-Difference or "JND," (also called "difference threshold" or $\delta_C$), is defined as the absolute difference in concentration required for detection of change from the initial concentration. Weber's Law (defined for all stimulus modalities, not just olfaction), states that the JND is a constant proportion of the original stimulus magnitude, i.e., that the ratio $k=\underline{\delta}_C$, where C is a constant.

A primary goal of the Smell Engine described herein is to be able to produce odors at an appropriate resolution across the perceivable concentration range of OMs—high enough to replicate the smallest detectable changes in concentration.

To allow for controlled changes in perceived odor intensity, the described system digitally parameterizes the physical properties of the OMs that are stored in the liquid phase in identical vessels. Parameters include vapor pressure, liquid-phase density, and molecular weight. From these values, the system computes the partial pressure of the vapor phase for each OM at steady-state within an associated vessel. Mixing these OMs produces an N-dimensional "Odor Mix" Vector, where N is the number of unique odorants in the virtual space.

Figure 3A:
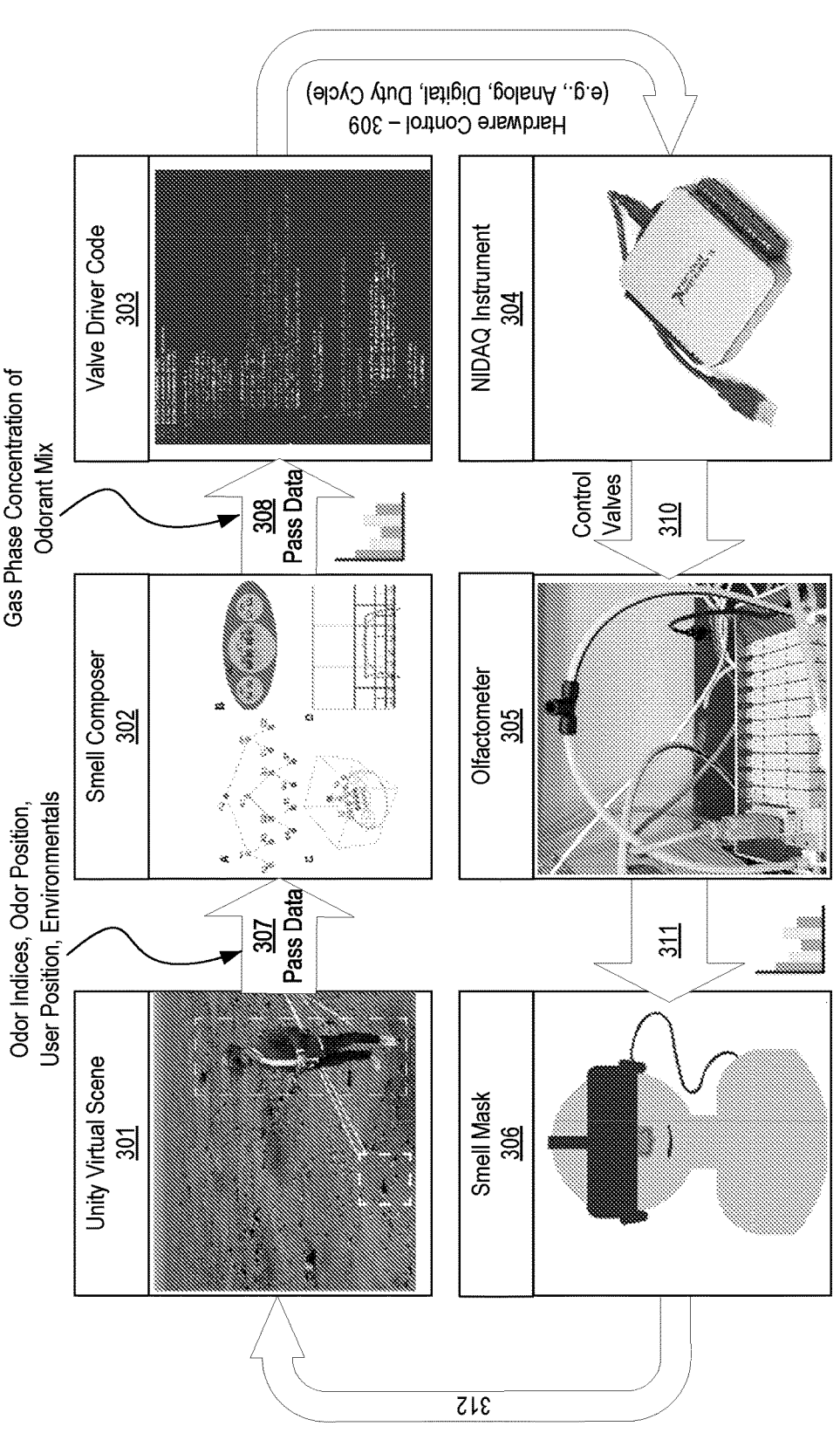
FIG. 3A depicts an exemplary sequence diagram 300 of an experience using the augmented reality olfactory delivery engine, in accordance with described embodiments.

FIG. 3A depicts an exemplary sequence diagram 300 of an experience using the augmented reality olfactory delivery engine, in accordance with described embodiments.

As shown here, Unity virtual scene 301 may be a virtual scene developed using augmented reality (AR) development framework Unity 205. Unity virtual scene 301 may include the placement of a user-occupant 313 wearing smell mask 306 and a virtual smell object 314. The augmented reality olfactory delivery engine may gather data 307 from Unity virtual scene 301 such as odor indices, odor position, user position, environmental data, etc. According to certain embodiments, such data 307 may be acquired via NIDAQ API 220 and received by smell composer 302.

Smell composer 302 may issue parameters and commands to valve driver 303, for example defining a desired gas-phase concentration of odorant mix 308 and call the function IssuevalveDutyCycies 211 to produce a desired odorant mixture.

Valve driver 303 may then send hardware control data 309 to NIDAQ instrument 304. According to certain embodiments, hardware control 309 may be analog, digital, or duty cycle-based. NIDAQ instrument 304 may manipulate control valves 310 of olfactometer 305, to pressurize and release 311 a desired gas-phase concentration of odorant mix 308 into 312 the Unity virtual scene 301 via smell mask 306 worn by user-occupant 313. This simulates the perception of a desired odor associated with virtual smell object 314 within the senses of user-occupant 313.

Figure 3B:
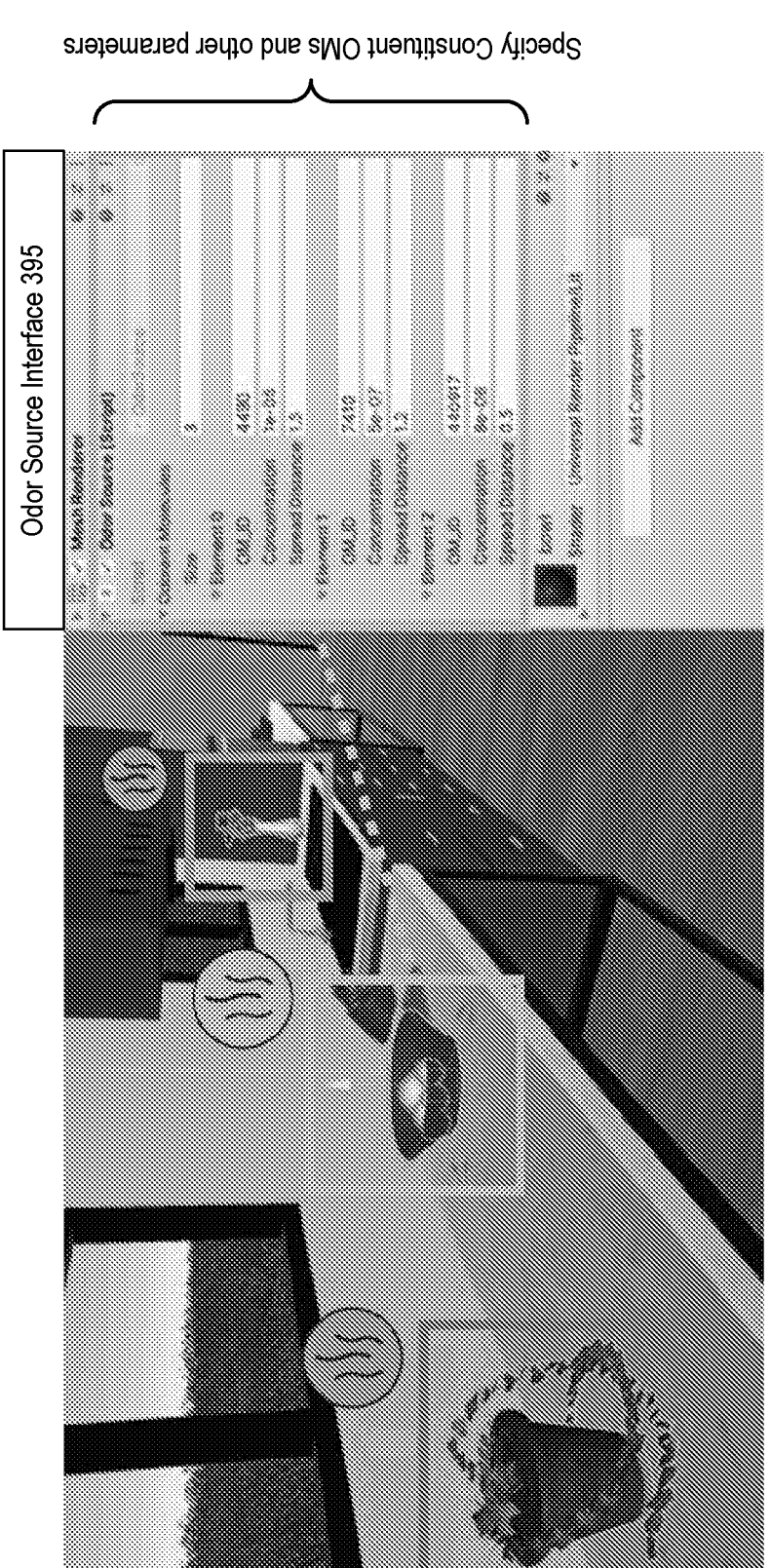
FIG. 3B depicts an exemplary Smell Composer and its Odor Source interface, in accordance with described embodiments.

FIG. 3B depicts an exemplary Smell Composer and its Odor Source interface, in accordance with described embodiments. As shown here, using the Smell Composer's Odor Source interface, a designer can create an odor mixture by specifying constituent OMs, along with the OMs' relative peak concentration and relative spread.

Figure 3C:
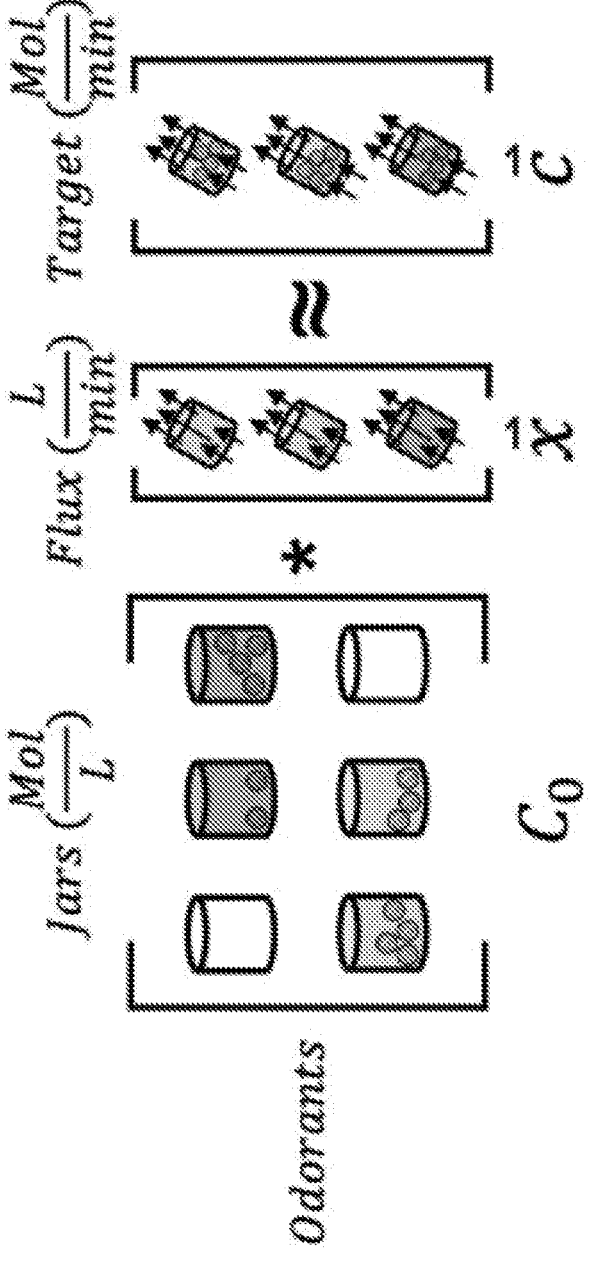
FIG. 3C depicts a set of available odorant concentrations $C_0$, for use with the Smell Controller, in accordance with described embodiments.

FIG. 3C depicts a set of available odorant concentrations $C_0$, for use with the Smell Controller, in accordance with described embodiments. As shown here, the Smell Controller determines an optimal flux j in olfactometer scheduling that approximates the target Odor Mix Vector with an achievable Odor Mix Vector c.

FIG. 3D depicts presents equation (1) for use with described embodiments.

Figure 4A:
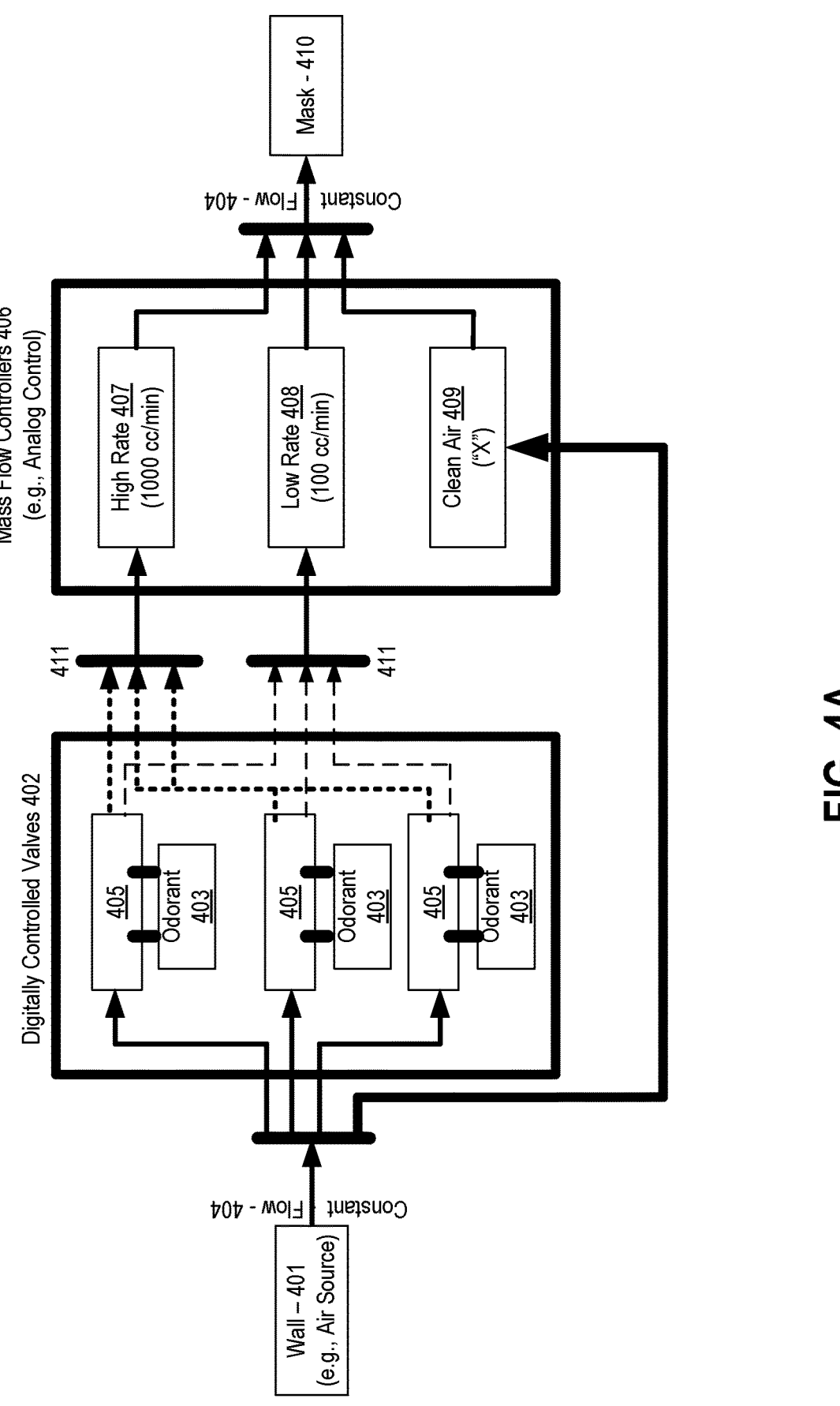
FIG. 4A depicts an exemplary smell engine component diagram 400, in accordance with described embodiments.

FIG. 4A depicts an exemplary smell engine component diagram 400, in accordance with described embodiments.

As shown here, valves 402 are digitally controlled and wall 401 of smell engine may adjust pressure to maintain a constant flow rate 404 on odorants 403, which may be in liquid form with varying viscosity, such as an oil or extract. According to certain embodiments, odorants 403 are desired odorant mixtures prepared via valve driver 210 overseeing the execution of the function issuevalveDutyCycles 212 to digitally manipulate valves 402 pneumatically connected across manifold assembly 103.

Through pressurization process 405, odorants 403 are pressurized from a liquid-like phase into a gas-phase. According to certain embodiments, following pressurization process 405, odorants 405 may be channeled 411 towards either high rate (1,000 cc/min) channel 407 or low rate (10 cc/min) channel 408 of mass flow controllers (MFCs) 406. Mass flow controllers 406 may be controlled in an analog fashion. Clean air (x) may flow through its own channel 409.

According to certain embodiments, high rate channel 407, flow rate channel 408, and clean air channel 409 flow together with constant flow 404, carrying odorants 403 towards smell mask 410 for emission into virtual scene 301 and sensation by a user-occupant 313.

Odor Delivery System (Olfactometer): The described odor delivery system is a dynamic dilution olfactometer which provides a consistent airflow source that mixes OMs by combining the independent vapors from one or more vessels attached to a manifold. According to such embodiments, the olfactometer operates with a fixed set of odorants distributed across a number of sealed vessels, capable of producing many combinations of odor mixtures. The specific odorants and concentration in each vessel must be determined in advance, but linear combinations can be delivered during the operation phase.

The olfactometer directs clean airflow through the headspace of vessels containing liquid odorants in an odorless solvent (light mineral oil). This is achieved using a manifold of programmable, digital solenoid valves and analog programmable mass flow controllers to provide precise flow rate through each vessel headspace, thus creating the OM composition of the resulting mixture. A standard output flow rate of 10 L/min is used for the olfactometer, formed from the combined output of the OM manifold and a clean air stream to achieve proper dilution. Solenoid valves direct the output of each vessel pneumatically to one of three paths: high flow (A), low flow (B), or no flow (refer to FIG. 4A). Each valve is programmed such that each odor "frame" can contain any combination of state (Analog Control), (Digital Control), and Vacuum occupancy times that sum to the length of the frame (as shown here, 1 second). This forms a duty cycle of active and inactive OM contribution.

The exemplary system uses Mass Flow Controllers (MFC) to govern the low flow and high flow paths, recomputed in each frame within each MFC's operating range. Each MFC is chosen to provide precise flow rate control in a different concentration regime (A: 1-1000 mL/min; B: 0.01-10 mL/min; Final: 0.01=10 L/min), and by combining them a high dynamic range is achieved. The total flow rate is held constant to produce a consistent user experience with constant air pressure. Total control over the composition of the Odor Vector—the time-varying concentration of each OM—is thus achieved by continuously and jointly setting the duty cycles of each solenoid valve and the flow rate set-points of each MFC.

The odorous air output from the olfactometer is combined with clean air 409, then fed into a nose mask 410 that nests/clamps over the user's nose. Refer also to the smell mask 306 as depicted at FIG. 3A. Attached to the bottom outlet of the nose mask is a vacuum that sucks odorous air from the nose mask every other 500 ms. If no odorous air is outputted from the olfactometer, then the user is continuously fed clean air. Altogether, the system directs constant airflow with partial flow rates over valve devices adjusted by a set of MFCs, recombined and fed into a nose mask worn on the user's nose.

System Design and Methodology:

The Smell Engine provides olfactory stimuli that are: i) spatially varying, ii) diverse and granular in user-perceivable strength, and iii) contextual to the virtual environment. To this end, the Smell Engine uses three primary components—as illustrated in FIG. 2A: a Smell Composer 215 for design of virtual odor spaces, a Smell Controller for runtime computation of virtual odor mixes (see e.g., Unity 205 at FIG. 2A which calculates concentrations 206 and sends the desired concentrations 207 to the next component), and a Valve Driver 210 to control hardware to produce physical odor mixes.

Designer Tools for Odor-Infused Environments: Designers are enabled to create a virtual scent-filled environment consisting of odorous objects and regions, through the use of the Smell Composer framework. This framework specifically enables designers to specify Odor Source instances and locations. Designers do this by attaching Odor Source components to virtual objects, describing odor identity and propagation characteristics as attributes of the Odor Source. Odor Sources can also be attached to the entire virtual space, creating an "ambient smell" to the environment. The game engine can also modify Odor Source attributes at runtime, e.g., changing the odor strength over time, or swapping in different scents in response to a user button press. The designer can also modify Odor Source attributes at runtime, e.g., changing the odor strength over time or swapping in different scents in response to a user button press, via scripted events in the Unity Game Engine. Altogether, the Smell Composer framework provides a creative palette for designers to prepare virtual scenes imbued with odors.

An Odor Source interface further allows the entry of the relative peak concentrations of odorant molecules (OM), creating the "scent profile" of the scent. Designers can also use the interface to specify the relative spread of each constituent OM, thus allowing the scent profile to change with distance. According to certain embodiments, so as to identify OMs and reliably discern the chemical and physical properties of OMs, the Smell Composer interfaces with PubChem, which is an open chemistry database created by the National Institutes of Health. Using PubChem, the Smell Engine obtains each requested OMs vapor pressure, molar density, and molecular weight. Combined with the user-specified liquid volume of each OM per jar, the Smell Engine then determines each jar's vapor concentration by calculating the partial pressure and molarity of each present OM. By integrating PubChem's vast library of virtually identifiable OMs with the Odor Source interface, Smell Engine equips designers to create and modify virtual odor recipes using a wide range of olfactory specifications.

The odor source's spread distance and max concentration parameters allow a designer to specify diffusion properties of the odor, i.e., when and how much of the odor strength is to diffuse. Analogous to virtual audio stimuli in a Game Engine, changing the max concentration and spread of an Odor Source component is similar to changing the volume and spread of an Audio Source component. To elongate or shorten the gradual change of odor strength, designers adjust the spread distance parameter. If one constituent odorant of an odor source's set of odorants is more dominant in intensity over others, designers can modify the max concentrations to reflect this. By adjusting these parameters, designers can choreograph olfactory stimuli in virtual experiences such that odor strength becomes adaptive to user proximity. Using such a composition of odors, the scent of a lemon bowl, for example, will get stronger as a user approaches the fruit.

Following the audio stimuli analogy, odor sources function similarly to audio sources in that they can be dynamically positioned within the virtual environment, anchored to specific areas/regions, and assigned to game objects. Should the designer want an environmental smell for the virtual space with no associated game object/model, they can create an Odor Source instance fixed to the camera. If the designer wants an odor source to travel through the virtual environment, e.g., an NPC with an associated odor, they can assign an Odor Source instance to the moving game object.

Runtime for Mixing Odor Recipes at the Virtual Nose: With Odor Sources defined and instantiated at design time, the Smell Engine operates at runtime to aggregate all odor sources into a single odor mix vector at the user's virtual nose, which then is used to faithfully match the virtual odor composition with a physical odor composition. Similar to audio stimuli in a game engine, a Smell Mixer can be thought of as an Audio Listener; the Smell Mixer receives input from all stimuli sources, then renders the aggregate stimulus for the user to trigger hardware actuation. The Smell Controller may further determine an optimal flux in olfactometer scheduling that approximates the target odor mix vector with an achievable odor mix vector.

To determine the odor mix vector relative to a user's position, the Smell Mixer uses an atmospheric diffusion equation defined to spatially present odors in a virtual environment. The Smell Mixer emulates the aggregation of spatially-varying concentration profiles of the N molecular odorants, which are indexed by $i \in \{1,N\}$, as they present themselves through M virtual odor sources, indexed by $j \in \{1,M\}$. As the user moves farther from the odor source, modeled by their distance from the odor source, the concentration profile diminishes through atmospheric diffusion along a Gaussian relationship with odorant-specific $\sigma_i$ dispersion coefficients. Based on such modeling, the odor synthesis system aggregates perceived concentration of each odorant as a sum across all odor sources:

$$m_i = \sum_j c_{i,j} \, e_j^2 / \sigma_i^2.$$

Together, these concentrations form a Odor Mix Vector m of target odorant concentrations. With this Odor Mix Vector, scents of various programmable objects can naturally compete and combine before artificial synthesis.

Controller to synthesize physical OM recipe from virtual odor mix vector: According to described embodiments, the Smell Mixer transmits its calculated Odor Mix Vector to the Smell Controller, a subsystem process for configuring an olfactometer on-the-fly to delivering dynamically mixed odors. Given the Odor Mix Vector, the Smell Controller specifies a scheduled duty cycle of valve states to control odorant exposure times and Mass Flow Controller (MFC) flow rates to regulate the airflow volume through the valves. To determine when and how much of an odorant must be diffused through the system's airflow, the Smell Controller calculates the amount of flux needed to achieve a target concentration using a set of variables that are representative of the system's physical components.

A matrix representing the available set of odorant concentrations in each jar is defined as $C_0$. The term z is defined as the flux, and the term 8 is defined as the target concentration. To represent flow rates and valve duty cycles, $f_A$ is defined as the flow rate of MFC A, and $f_B$ as the flow rate of MFC B, with the term i as the index of a jar, and n as the number of jars. The terms $w_{iA}$ and $w_{iB}$ are used as the occupancy time in ms of valve i in state A and state B, respectively. The flux $y_i$ going through a jar i can thus be calculated using equation 1 as set forth at FIG. 3D.

As noted previously, the hardware capabilities of the olfactometer's components have various constraints that manifest as parameter constraints to an optimization function which operates to approximate the flux. An odor table was used to pre-compute solutions for a different flow rate and duty cycle combinations within the available constraints. The odor table contains 48 concentration setpoints evenly spaced on a logarithmic scale ranging from [1 nanomolar, I micromolar], eight MFC flow rate setpoints spanning across three orders of magnitude [0.1 cc/m to 1000 cc/m], and 18 valve occupancy times, evenly spaced on logarithmic scale, occupying up to 1 second. Organized as a KD Tree, the odor table determines which combinations of olfactometer flow rates and duty cycles over the OM odorants in the jars that generate the achievable Odor Mix Vector that approximates the target Odor Mix Vector from the Smell Mixer.

Olfactometer hardware control for odor synthesis: Given the Smell Controller's scheduled valve duty cycles and MFC flow rates, the Valve Driver executes the schedule using multifunction I/O modules provided by National Instruments. The Smell Controller's schedule was converted into digital and analog control signals that were used by the system to direct the odorants' vaporized air-flow through a series of tubes that are connected to the solenoid valves and MFCs, diffused into a nose mask, and sucked through using a continuously running vacuum.

The Valve Driver interfaces through the NIDAQmx API (refer to element 220 at FIG. 2A) to issue multiplexed digital and analog signals that correspond to scheduled valve states and MFC flow rates. The Valve Driver issues valve duty cycles as 32-bit digital values; the first 16 bits represent high states, the lower 16 bits representing low states; zeros represent off states, while ones represent on states. The Valve Driver formats and converts issued MFC flow rates as a list of analog voltage values.

Evaluation Setup

System tests and user studies were conducted to evaluate the effectiveness of the Smell Engine in delivering olfactory stimuli of varying odor strengths. For the system tests, a photo ionization detector (PID) was used to evaluate the precision in which the Smell Engine synthesizes odorants at desired concentrations. The user studies evaluated how well the system helps to determine a subject's odor sensitivity levels and how the approach improves a user's ability to navigate virtual worlds using olfactory cues. For the user studies, a total of 15 subjects (11 male, 4 female) were recruited to participate in the three-part study, contingent on their ability to perceive all odors presented. The user studies identified: 1) the user-perceived latency for odor delivery: 2) how coarsely or finely users can identify different odorant strengths; and 3) how effectively users can localize virtual odor sources. No user subject reported any history of a medical condition that reduced their sense of smell.

Odorant/Scent Selection: For testing, ethanol was used because it provides a strong and consistent PID response, and the kinematics (e.g., vapor pressure) of ethanol are similar to the selection of odorants. The odorant selection for user studies consisted of Acetophenone, Carvone, and D-limonene, as safe, readily accessible odorants. Generally, users reported that Acetophenone smelt sweet like berries, Carvone smelt like peppermint, and D-limonene smelt like oranges. Each odorant was prepared manually at different dilutions—10:1 for Acetophenone, 1:1 for Carvone, and 10:1 for D-limonene—using light, odorless mineral oil as the solvent. The odorants were loaded into glass jars attached by PTFE tubing to an aluminum manifold.

Odor Synthesis Precision

Trial Procedure: The experimental setup consisted of a push-to-connect pneumatic fitting that connects the odorous air, a vacuum, and the PID septum into the sealed-off outlet. To ensure reliable PID readings for each trial the following precautions were observed: 1) clean air was measured at a steady-state as a reference point, 2) testing waited for PID response to achieve steady-state for each target concentration or hardware configuration, and 3) clean air was measured again to account for sensor drift. Using this testing process, a series of experiments were conducted to vary the valve duty cycles and MFC flow rates to evaluate the relationship from the PID response. In the first experiment, the relationship between the PID response and valve duty cycle was evaluated by gradually increasing the relative valve occupancy time from 0 to 1000 ms in 100 ms increments. In each trial, the flow rate setpoint was increased by a fourth of its max capacity (i.e., [2.5 cc, 5.0 cc, 7.5 cc, 10.0 cc] for MFC B and [250 cc, 500 cc, 750 cc, 1000 cc] for MFC A).

Figure 4B:
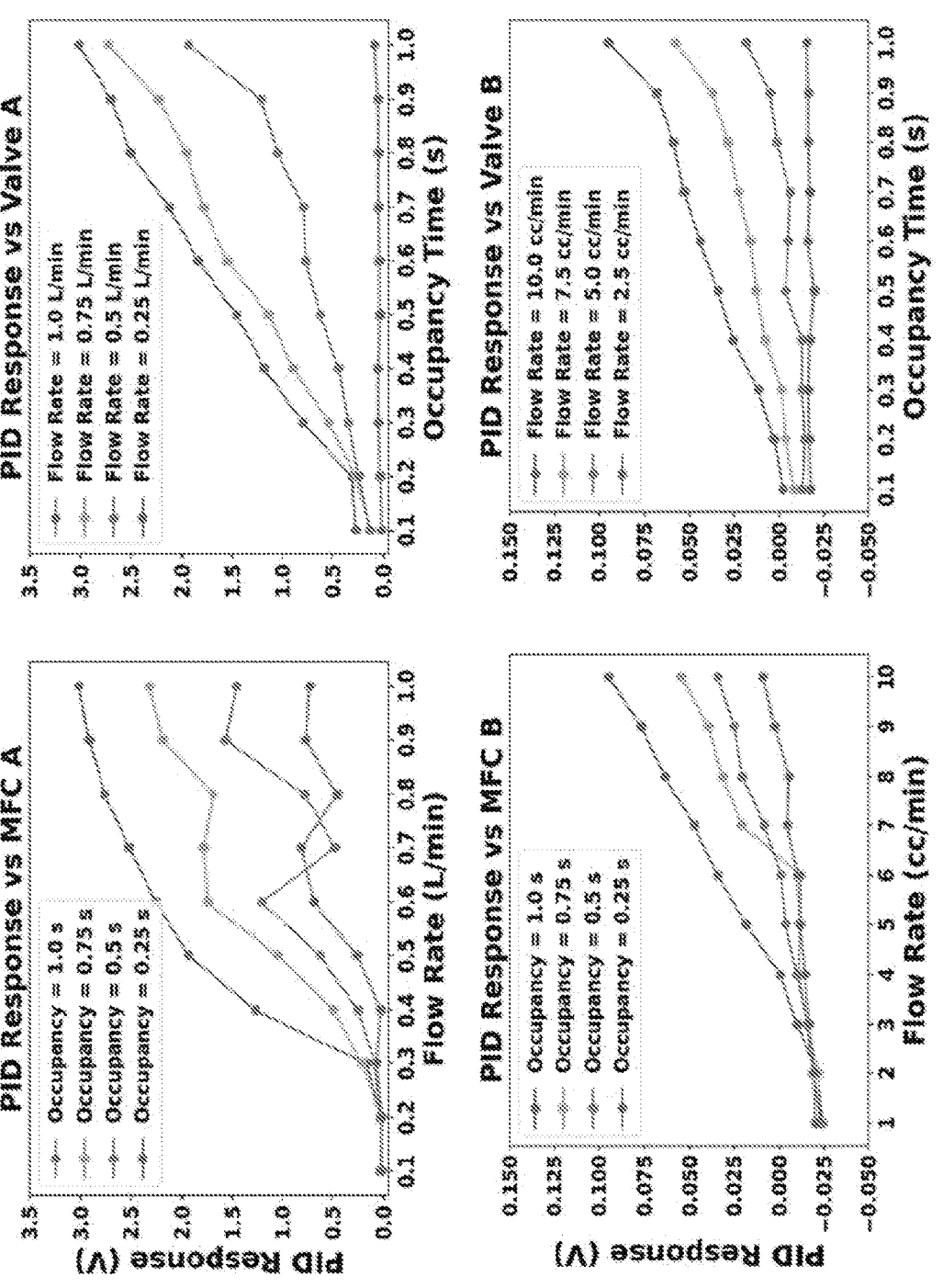
FIG. 4B depicts PID sensor readings for increased valve occupancy times and MFC flow rates, in accordance with described embodiments.

The carrier MFC supplements the remaining airflow needed to meet the constant flow rate target. In the second experiment, to understand the relationship between MFC setpoints and PID response, conducted a series of tests were conducted, incrementally increasing the MFC setpoint with different duty cycle configurations. For the last experiment, the precision of odor synthesis was evaluated over six trials. This experiment, tested 16 different concentrations, ranging from 1 picomolar to 1 micromolar FIG. 4B depicts PID sensor readings for increased valve occupancy times and MFC flow rates, in accordance with described embodiments. As shown here, adjustments were made to MFC A flow rate (top left), MFC B flow rate (bottom left), relative valve occupancy time in a high flow rate state (top right), and in a low flow rate state (bottom right) to generate the graphs.

Results: The results presented at FIG. 4B illustrate a relatively linear relationship between PID sensor readings and increased valve occupancy times or increased MFC flow rates. Illustrated with the subplots, it may be observed that lower flow rates achieve a high-precision range of 10.0 mV, whereas higher flow rates achieve a coarse range of 3 V. The ratio difference for PID sensor readings in a high versus a low state is consistent with the ratio difference of airflow between MFC A and MFC B, an approximate 3 order of magnitude difference. With the occupancy subplots in FIG. 4B, an approximate 1:4 ratio was observed for a quarter usage of an MFCs max flow rate compared to the max flow rate of the MFCs. Similarly, for the flow rate subplots in FIG. 4B, an approximate 1:4 ratio was observed for a quarter valve duty cycle compared to the max valve duty cycle. As seen with all data points in the subplots, the combination of increased MFC flow rates and valve duty cycles results in a higher PID response, presenting a monotonically increasing relationship.

Figure 4C:
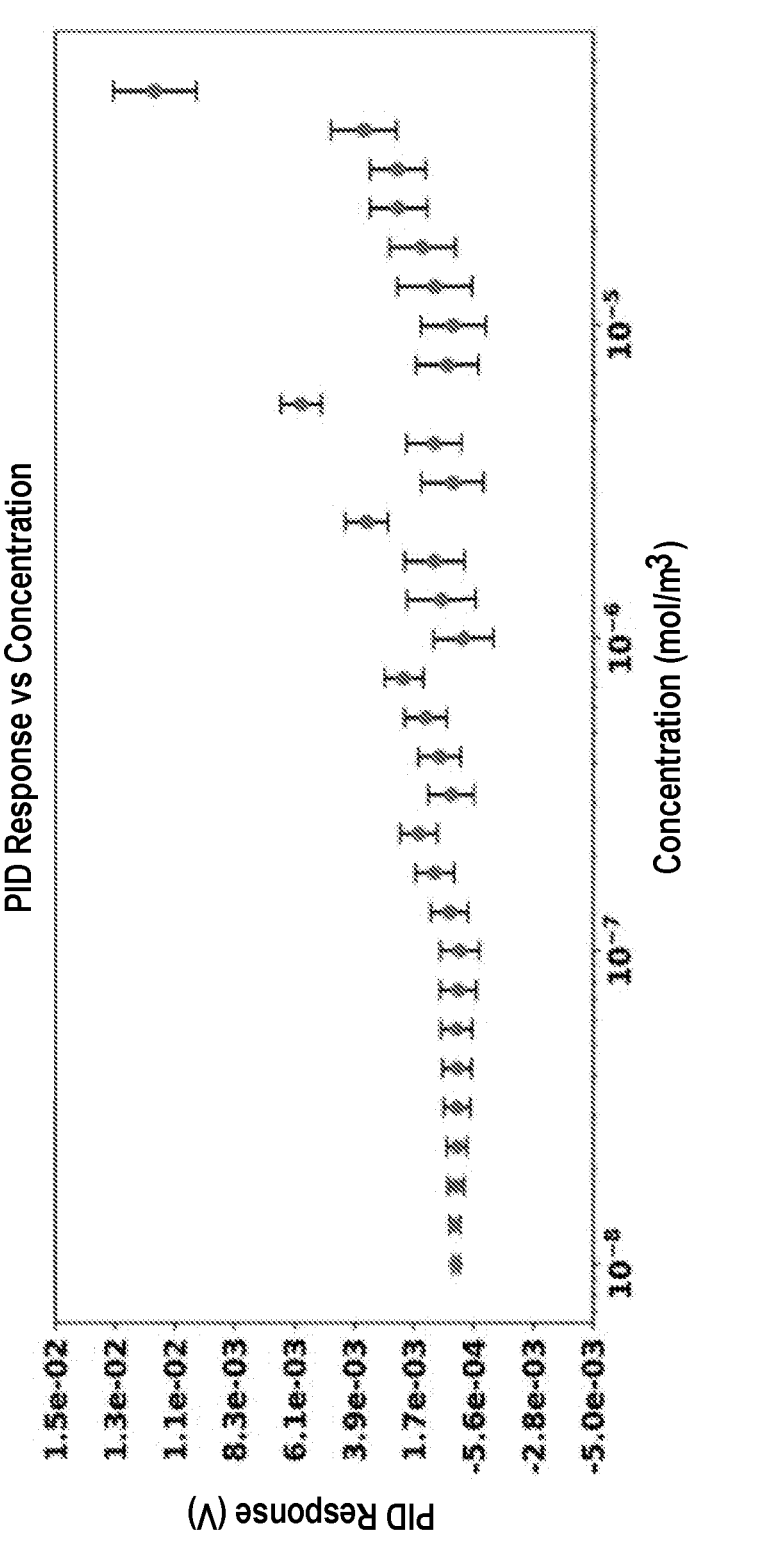
FIG. 4C depicts PID sensor readings across 6 trials for entire concentration range, demonstrating increasing variation with larger concentrations, in accordance with described embodiments.

FIG. 4C depicts PID sensor readings across 6 trials for entire concentration range, demonstrating increasing variation with larger concentrations, in accordance with described embodiments.

As shown here, the PID sensor readings for target concentrations comprising varied valve duty cycles and MFC flow rates. From this data, a roughly increasing PID response is observed with higher concentrations. The observed plateau in PID response is in accordance with the previous system tests, validating a roughly linear relationship within the picomolar range.

Figure 4D:
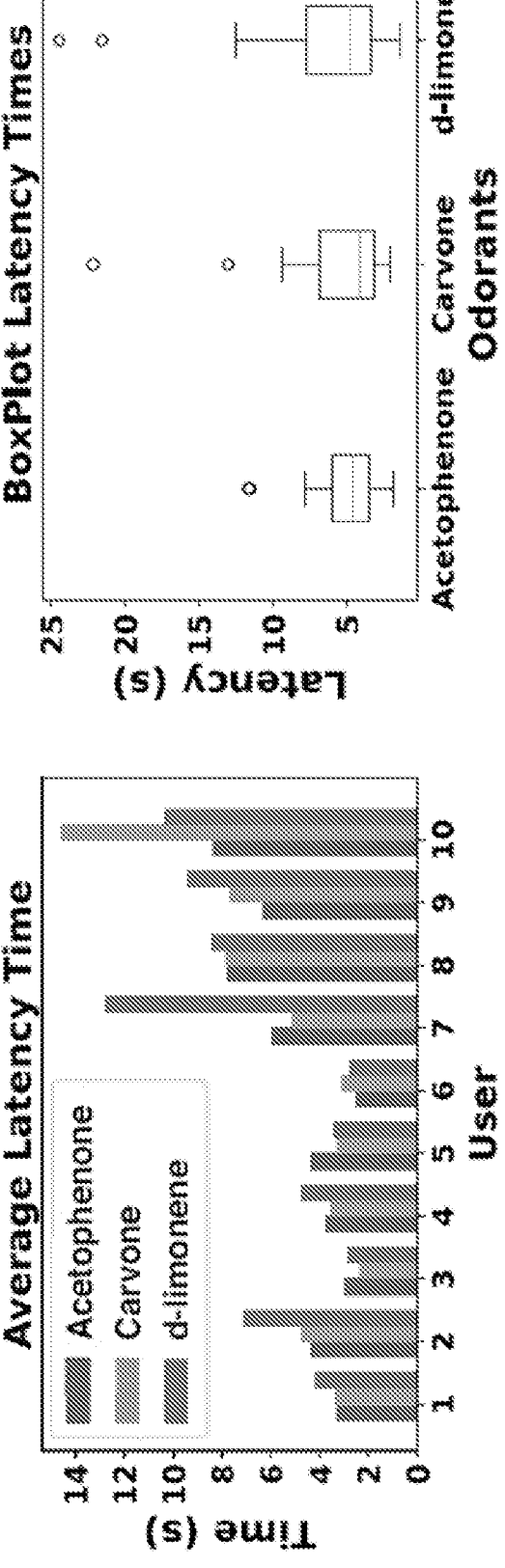
FIG. 4D depicts user-perceived latency for each odorant, in accordance with described embodiments.

FIG. 4D depicts user-perceived latency for each odorant, in accordance with described embodiments. Subjects that could not perceive the odor are shown as anomalies.

User Study 1: User-Perceived Latency

User-perceived latency of the Smell Engine's odor diffusion capabilities were evaluated. For this experiment, each odorant was diffused at its max concentration, i.e., max flow rate and valve duty cycle. In addition to measuring the user-perceived odor diffusion latency, the experiment was used as a screening session to determine whether a subject can smell the odorants. If a subject does not have sensitivity to the odorants, then that participant did not proceed with the rest of the study. This excluded 5 out of the 15 participants.

Trial Procedure: For this study, users trigger a clicker to activate olfactory stimuli and trigger it again when olfactory stimuli are perceived. This experiment is repeated three times for each odorant, generating three latency measurements for each odorant. If the subject cannot perceive the stimuli within 15 seconds for 2 out of 3 trials for any odorant, then it was concluded that the subject cannot perceive the stimuli.

Results: Users perceived the system-generated odors from 2.5 to 10 seconds after the virtual triggering of the odor, (with two outliers at 12 and 14 seconds). The variation seemed to be user specific, i.e., some users perceived odors faster than other users. Among the users, the average user-perceived latency of the system's odor diffusion capabilities is approximately 5.7 seconds. Despite having a small sample size, an ANOVA was conducted for multiple comparisons and found that the influence of odor type on user-perceived latency was not statistically significant ($p>0.05$). As shown at FIG. 4D, it was observed that some users perceive smells faster than others. Additionally, it was observed that 75% of the user subjects perceived all diffused instances of the odorants within a 10-second time frame, depicted here. Four (4) subjects could not perceive at least one of the odorants within the threshold timeframe; these subjects did not move forward with the rest of the study. In a future study, additional demographic info may be collected with testing of more familiar and less familiar smells.

User Study 2: Just-Noticeable-Difference Odorant Concentration Strengths

A second study sought to understand how effectively the system can help determine user-sensitivity levels for specific odors by measuring the user-reported just-noticeable-difference (JND) values for the olfactory stimuli. As described above, a TND value quantifies the amount by which a change in stimulus intensity produces a noticeable variation in the human sensory experience. This information is invaluable as it helps to better understand the relationship between olfactory stimulus intensity and user perception. If the system can generate odor concentrations that are more granular than the average user perceivable JND values, then a screening system can be devised to determine a subject's odor acuity level. Such a capability would be especially useful in modeling subject perception of olfactory stimulus overtime.

Realizing these opportunities, user-reported minimum odor strengths were investigated for each odorant and JND concentration values relative to different baseline concentrations: 0 molar, 10 picomolar, 100 nanomolar. For the second baseline, evaluation started with 10 picomolar because of the limited achievable concentration strengths of the odorants. For this first study, it is hypothesized that a user using the system can identify a subject's JND odorant concentration value relative to the starting concentration value.

Trial Procedure: To discover JND concentration values, a staircase procedure was implemented to identify each user's perceptual threshold. The staircase procedure is an iterative process that, given a starting stimulus strength X, will increase/decrease the intensity of the stimulus X by a delta, y, until a subject specifies a perceived change in stimulus strength. After the subject perceives the change in stimulus strength three times, the recorded X+y threshold values were averaged. The result is a user-specific JND value such that X±y is not differentiable from X if y<JND and is differentiable from X if y>JND. The study was conducted with ten subjects, none of whom reported any former medical issues that would influence their sense of olfaction.

For each trial in the study, the subject was presented with the baseline concentration X, along with the increased odor concentration Y, in a randomized order. The participant was then prompted to confirm whether they noticed a difference in odorant concentration strength. At the start of each odor concentration, the subject places the nose mask and is able to sniff for up to 10 seconds. After concentrations X and Y are presented to the participant, they were prompted to confirm whether they noticed a difference in odorant strength. If a user subject reports no difference in odor strength, Y continues to increase by a concentration value, h, which is a multiple of the baseline. Should the user subject report a difference in odor strength, then h is halved and Y is decreased by h to determine a more granular JND value. Once a subject reports a difference three times, the Y concentrations are averaged and the result is recorded as the subject's JND value.

For the first trial, the baseline is no concentration strength (X=0) and the starting concentration is 10 picomolar ($Y=10^{-11}$). For the second trial, the baseline is 50 nanomolar ($X=5 \cdot 10^{-8}$) and the starting concentration is 60 nanomolar ($Y=6 \cdot 10^{-8}$). For the third trial, the baseline is 10 picomolar ($X=10^{-11}$) and the starting concentration is approximately 13 picomolar ($Y=1.316^{-11}$). This procedure is repeated for all odorants.

Figure 4E:
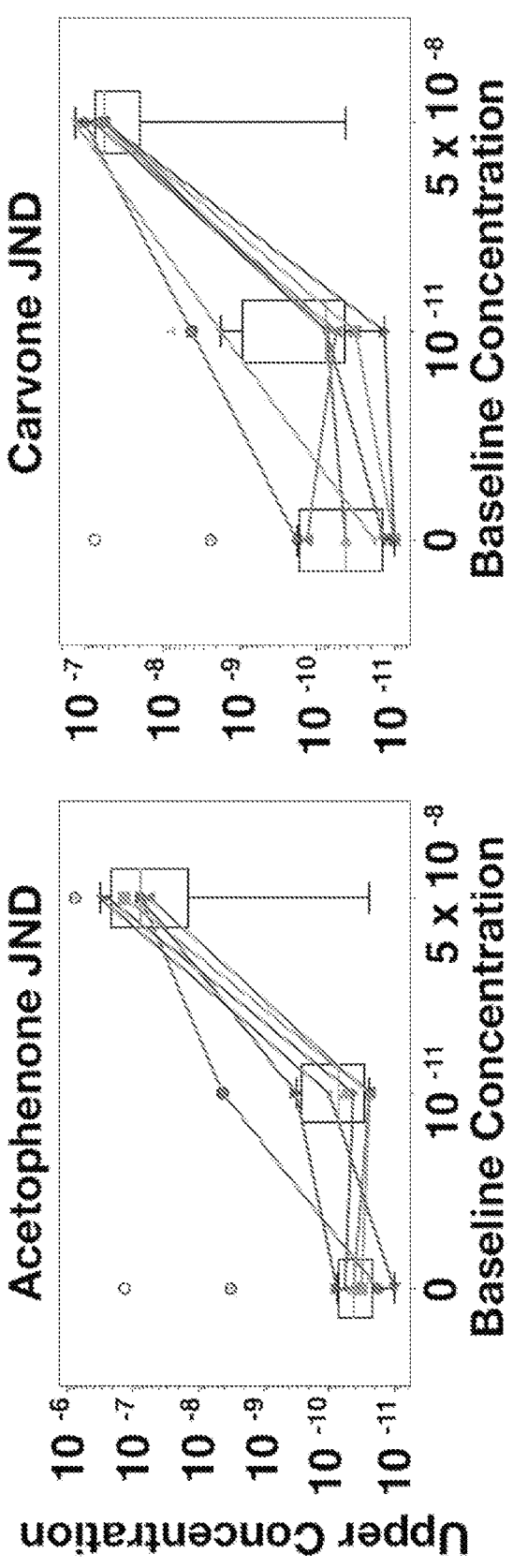
FIG. 4E depicts user-perceived JND results for different relative baselines, in accordance with described embodiments.
Figure 4E:
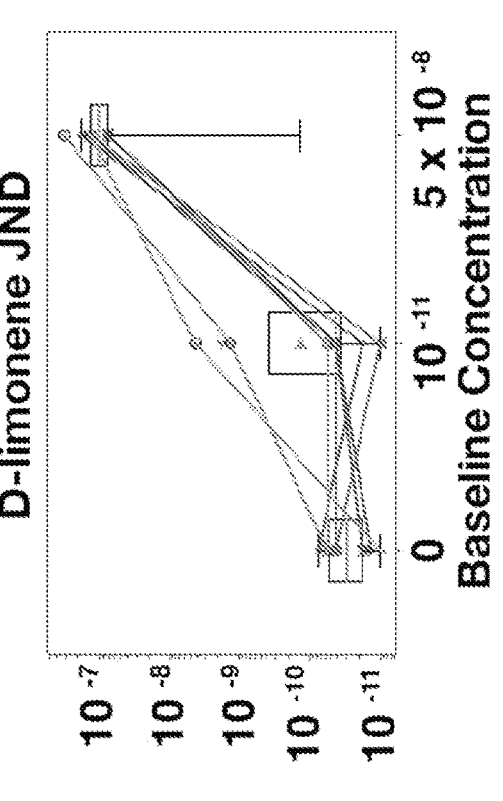

FIG. 4E depicts user-perceived JND results for different relative baselines, in accordance with described embodiments. Each color represents one of the ten different users.

Results: The results suggest that the Smell Engine can help identify a subject's JND relative to the starting odorant strength. The box-and-whiskers plots in FIG. 4E visualize the variance in JND results for the different baseline concentrations. From this data, it was found that participants were less sensitive to changes in strength for 1-limonene compared to the other odorants, suggesting that the Smell Engine can be used to identify how perceivable an odor is for individual users or groups of users. FIG. 4E illustrates how subject JND values changed across trials. Because some subjects did not perceive a change in strength three times, there may be no connection between some baseline trials.

Consistent with the Weber-Fechner Law, it was observed that the level at which users perceive a change in stimulus intensity is proportional to the initial stimulus intensity. For example, the general distribution of user-reported JND values for the clean air baseline is more sensitive than at the 10.0 picomolar baseline trial. FIG. 4E shows that user-reported JND values are small when starting with a lower baseline concentration (e.g., 0, $10^{-11}$) and large when starting with a higher baseline concentration (e.g., $5 \times 10^{-8}$). Generally, it was found that the average JND value for all odorants is within two orders of magnitude relative to the baseline. In a future study, user-reported JND values may be investigated with more baseline concentrations spanning multiple orders of magnitude.

Illustrated in FIG. 4E, varying distributions of user-reported JND values for each odor and their respective baseline concentrations were observed. The variation of user-reported JND values suggests that the system can produce perceivable odor concentrations that span multiple orders of magnitude. Additionally, these distributions demonstrate the systems ability to generate concentration strengths that are more granular than the JND values.

From FIG. 4E, which illustrates how subject JND values vary relative to the baseline, it was found that several participants became more sensitive to granular changes in odor strength. For example, when comparing the 10.0 picomolar and clean air baseline trials, occasional instances are seen where user-reported JND values became finer. This finding motivates the potential of improving a subject's ability to identify changes in odorant strength over time. In a future study, exposure to specific odors over time influences a subject's sensitivity to the smell may be observed.

Interestingly, in some trials where the concentration baseline was large, subjects could not perceive changes in odorant strength despite noticing changes in stimulus strength for a lower baseline. Additionally, in some instances, subjects could not perceive a change in stimulus strength nor perceive the odorant itself, resulting in a significant variance of JND values. For example, with Carvone and D-limonene, the median is approximately 100 picomolar for test trials involving the picomolar and clean air baselines, suggesting that the outliers are pulling up the 75th percentile. For test trials that use the picomolar and clean air baselines, it was found that the distribution is larger than the trial that uses 50.0 nanomolar as the baseline.

User Study 3: Localizing Virtual Odor Sources

Another study determined the extent to which the system improves a user's ability to localize odor sources in a virtual environment compared to existing trigger-based solutions. With this study, subject accuracy in correct odor localization was measured using two different odor delivery methods. This approach used the dynamic odor delivery method, concentration is a function of distance, gradually getting more potent with user proximity. By contrast, with trigger-based odor delivery, the concentration is fixed and activated when the subject is within a 1.8 meter distance. Because during the pilot studies, most users would only start registering the dynamic delivery at 1.8 meter out, the 1.8 meter radius was set so that both the trigger and dynamic delivery methods would have the same radius of initial detection. For this study, it was hypothesized that there is a difference in the probability of correctly localizing an odor source between the odor delivery methods previously described, such that the dynamic delivery method yields improved accuracy.

Figure 4F:
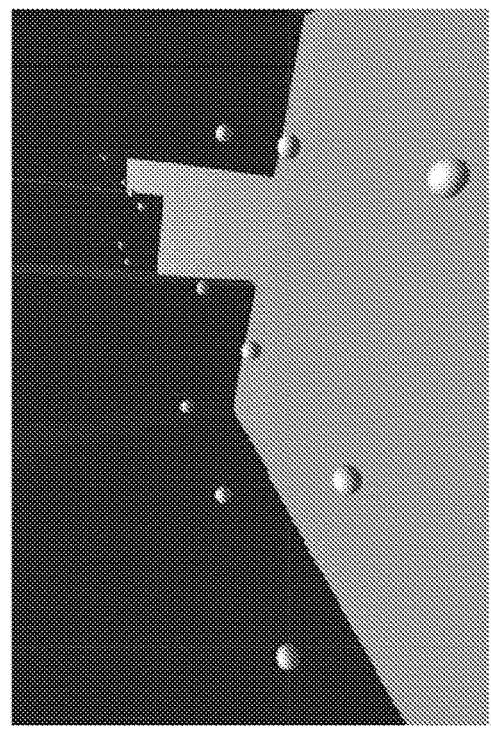
FIG. 4F depicts the manner in which a subject navigates and sniffs around an environment that consists of 3 rooms with 9 spheres, in accordance with described embodiments.
Figure 4F:
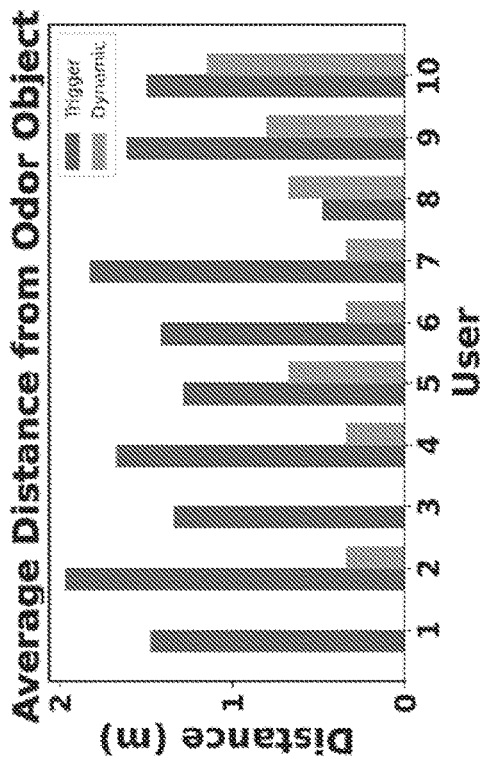
Figure 4F:
Figure 4F:
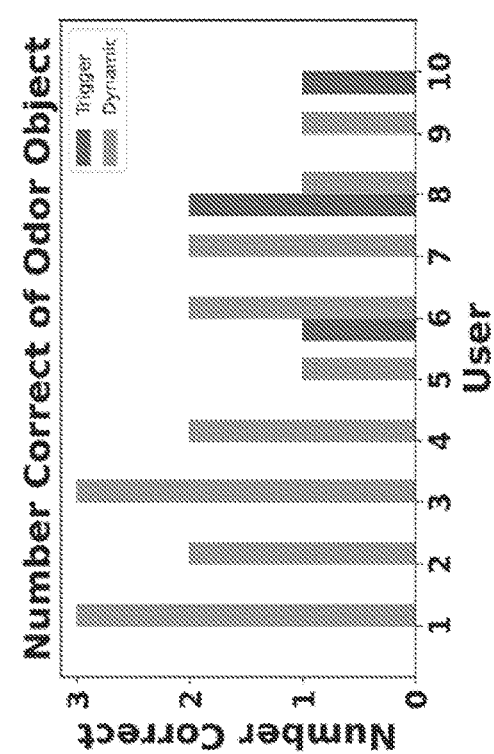

FIG. 4F depicts the manner in which a subject navigates and sniffs around an environment that consists of 3 rooms with 9 spheres, in accordance with described embodiments. As shown here, one of the 9 spheres is an odor source (top row). For each user, the number of correctly identified odor sources was counted and the average distance to the odor source selection was determined using two different odor delivery methods (bottom row).

Trial Procedures: The experimental design for this study consists of two trials in which the subject is prompted to correctly identify all odor sources in the virtual environment within a five-minute time frame. Both trials consisted of three rooms that each contained an odor source, as illustrated in FIG. 4F.

The study adopted a within-subject design in which odor delivery method and odorant type were the independent variable, and both accuracy and proximity of odor source selection were the dependent variables. To ensure participants relied on olfactory cues, the VR environments were designed to consist of similar layouts, primitive shapes/objects, a limited color palette, and the same odorants. Because this study is intended to study odor localization and not odor mixing, each room only contains one odor source. For each trial, the location of the odor source was randomized.

Subjects reported familiarity with VR and reported no past signs of olfactory-related diseases or surgeries. Before the study, the proctor helped the user put on the VR HMD, positioned the nose mask for comfort, and briefed them on the task. Subjects went through a tutorial scene that explained navigation and selection controls. Illustrated in FIG. 4F, the subjects navigated the virtual environment to select and specify odorous objects. Throughout the time of each trial, the subject's location was recorded, object interactions/selections, and final selections. The participants completed a motion sickness questionnaire before and after the study. Additionally, the participants completed a questionnaire evaluating the ease of identifying an odor source for each odor delivery method.

Results: The main finding was that the dynamic-based odor delivery improved user accuracy in identifying virtual odor sources compared to the trigger-based approach. Using an ANOVA for multiple comparisons, it was found that the influence of the odor delivery method on accuracy and proximal selection was statistically significant ($p<0.05$).

Illustrated with FIG. 4F, a 43% average improvement was observed in accurate odor localization with the dynamic delivery method. The average accuracy was 13.3% for the trigger-based odor delivery method, while the dynamic-based odor delivery method was 56.6%. With trigger-based odor delivery, only 2 of the ten participants were able to accurately localize an odor source. With dynamic delivery, all participants correctly localized at least one odor source precisely.

From the charts in FIG. 4F (bottom row), it was found that participants were on average within 0.46 meters when attempting to localize the odor source with the dynamic-based delivery method. Using the trigger-based delivery method, participants were on average 1.45 meters off in odor source selection. With the detection threshold of 1.8 meters, it was found that compared to the trigger-based odor delivery method, participants were on average 55% closer in proximity for odor source localization with dynamic-based odor delivery.

Correlations were further identified between odor-specific JND values, latency measurements, and accuracy in odor localization with dynamic delivery. For example, only 20% of users accurately localized D-limonene, which was associated with the smallest distribution of JND values and the highest average detection latency. With Acetophenone and Carvone, which had a more diverse distribution of JND values, more than 70% of users accurately localized the smells.

The described system can thus be used to study the ability to detect, identify, and localize different odors for different user populations. When reviewing the post-study survey, it was found that the rated ease for localization with the dynamic-based odor delivery method was higher than the trigger-based odor delivery method. Several participants remarked that it was easier to localize the odor source with the dynamic-based odor delivery method. No users reported signs of motion sickness after both trials of the VR experience.

Discussion

The results of this evaluation suggest that the Smell Engine can generate changes in odor strength that are more granular than user detection thresholds. Additionally, the Smell Engine can help identify a subject's odor sensitivity levels and improve their ability to localize odor sources within a virtual environment.

According to certain embodiments, specially configured implementations may include mask-based and mask-less wearable olfactory display designs that meet a wider range of profiles to improve both comfort and functionality. Other specially configured implementations may include the ability to mix odors on the fly, for instance, by: i) applying an olfactory runtime technique for dynamic, on-the-fly odor mixing, ii) reducing latency in odor delivery by offloading on-device computation towards new wearable form factors, and iii) building a malleable software pipeline for odor diffusion to support various hardware designs (e.g., SAW atomizers, trigeminal peripherals). Each of these could be facilitated through, for example, the application of edge computing to accelerate software-hardware systems for real-time computation of physics-based modeling that adaptively respond to dynamic scenes and user movements.

Study Conclusions

A Smell Engine is therefore described which is capable of computing and delivering olfactory cues on the fly in a virtual reality environment and which offers significant opportunities for a range of olfactory needs. These include opportunities for odor-oriented training and education, as well as basic scientific research, e.g., investigating whether humans identify and classify odors based on statistical co-occurrence of odorants, or more complex societal questions around cultures around smell. Virtual augmentation with dynamic, temporally and spatially delivered olfactory cues offers novel opportunities for examining, leveraging, and enhancing human olfaction. To this end, the described Smell Engine is presented as a software-hardware framework that integrates olfactory stimuli into virtual environments such that the odor strengths are spatiotemporally varying based on user navigation and interaction.

The Smell Engine was evaluated through measurement-based PID system studies and a three-part user study. From the set of PID tests, it was found that the Smell Engine can generate coarse and granular changes in odor strength. The results of the user studies (N=10) suggest that the Smell Engine can help identify whether a user can perceive a specific odor and help determine what their detection threshold is for the specific odor. Additionally, it was found that the system can improve a user's ability to localize artificially generated odor sources within a virtual environment, as compared to existing trigger-based solutions.

Figure 5:
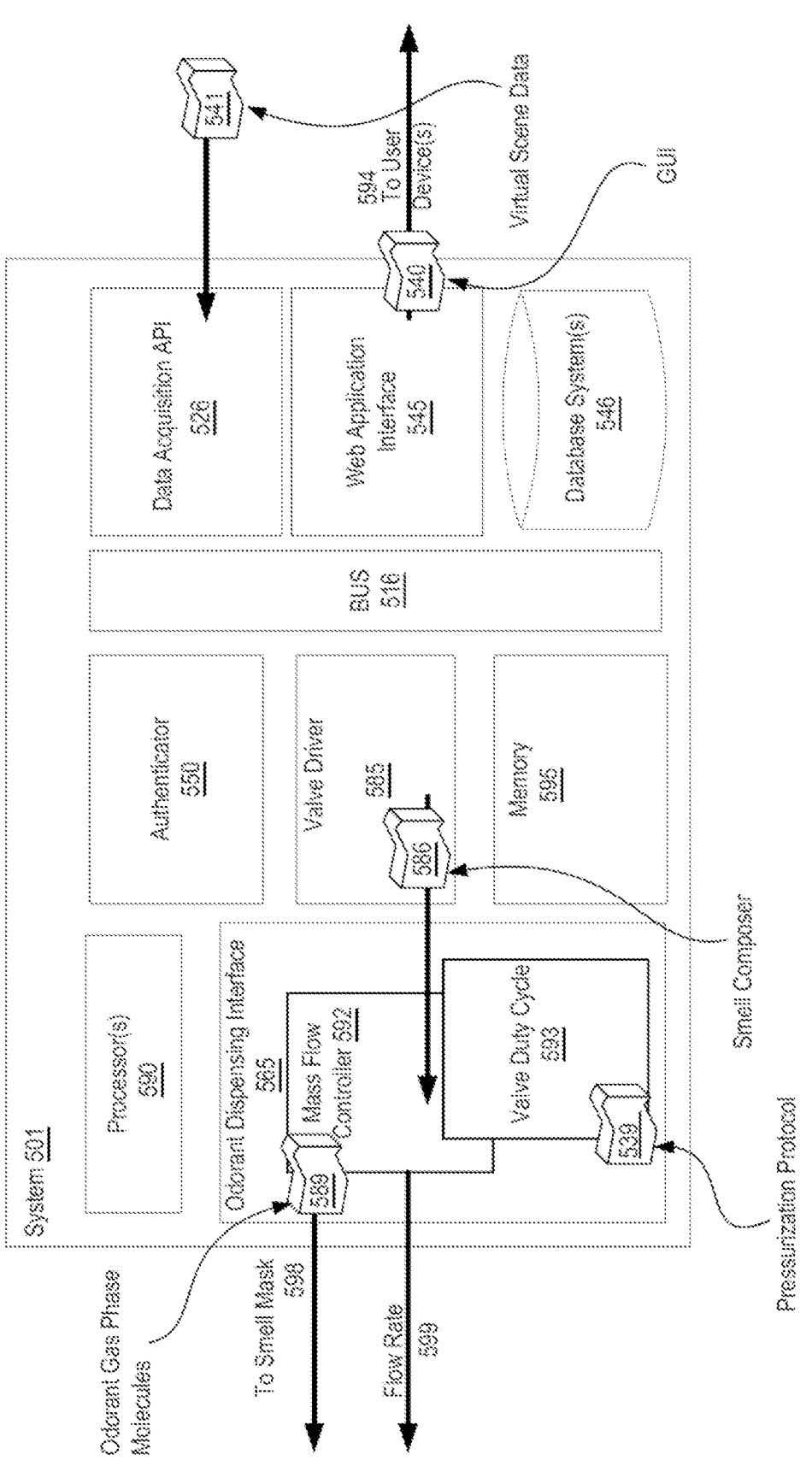
FIG. 5 shows a diagrammatic representation of a system within which embodiments may operate, be installed, integrated, or configured.

FIG. 5 shows a diagrammatic representation of a system 501 within which embodiments may operate, be installed, integrated, or configured.

In accordance with one embodiment, there is a system 501 having at least a processor 590 and a memory 595 therein to execute implementing application code. Such a system 501 may communicatively interface with and cooperatively execute with the benefit of remote systems, such as a user device sending instructions and data, a user device to receive as an output from the system 501.

According to the depicted embodiment, system 501 includes processor 590 and memory 595 to execute instructions at system 501. According to certain embodiments, instructions may be provided by a non-transitory machine-readable storage medium. System 501 as depicted here is specifically customized and configured specifically to implement an augmented reality olfactory delivery engine to simulate odors, in accordance with disclosed embodiments.

According to a particular embodiment, system 501 is further configured to execute instructions via the processor for acquiring data from a virtual scene 541 via a data acquisition API 526 based on one or more of: (i) positional information for an occupant, (ii) positional information for a virtual smell object, (iii) a desired odor index, and (iv) other environmental factors. Such a system is further configured to execute instructions via the processor 590 for mixing in real-time, via a smell composer 586 interfaced with an olfactometer issuing a valve duty cycle 593, one or more odorants according to a desired odor recipe including a desired odor concentration via a valve driver 585 commanding pneumatically-connected valves across a manifold assembly 103. The system is further configured to execute instructions via the processor 590 for producing a desired odorant mixture; pressurizing 539 the desired odorant mixture to gas-phase molecules 589 based on the valve duty cycle 593; directing, via a mass flow controller 592 setting desired flow rates 599, the gas-phase molecules into separate channels based on flow rates 599; combining the separate channels into a combined flow for dispensing from a smell mask 598; dispensing, via the smell mask 598, the gas-phase molecules 589 to a wearer of the smell mask 598, wherein the wearer of the smell mask 598 is the occupant in the virtual scene, wherein the dispensed gas-phase molecules 589 represent the virtual smell object; and simulating, via the dispensed 598 gas-phase molecules 589, a desired olfactory sensation within the senses of the wearer of the smell mask 598.

The web application interface 545 may further transmit output back to a user device or other requestor, for example, via GUI 540, or such information may alternatively be stored within the database system storage 546 of system 501.

According to another embodiment of system 501, a GUI 540 communicably interfaces with a user client device 594 remote from system 501 and communicatively interfaces with the system via a public Internet.

Bus 516 interfaces the various components of the system 501 amongst each other, with any other peripheral(s) of system 501, and with external components such as external network elements, other machines, client devices, cloud computing services, etc. Communications may further include communicating with external devices via a network interface over a LAN, WAN, or the public Internet.

Figure 6:
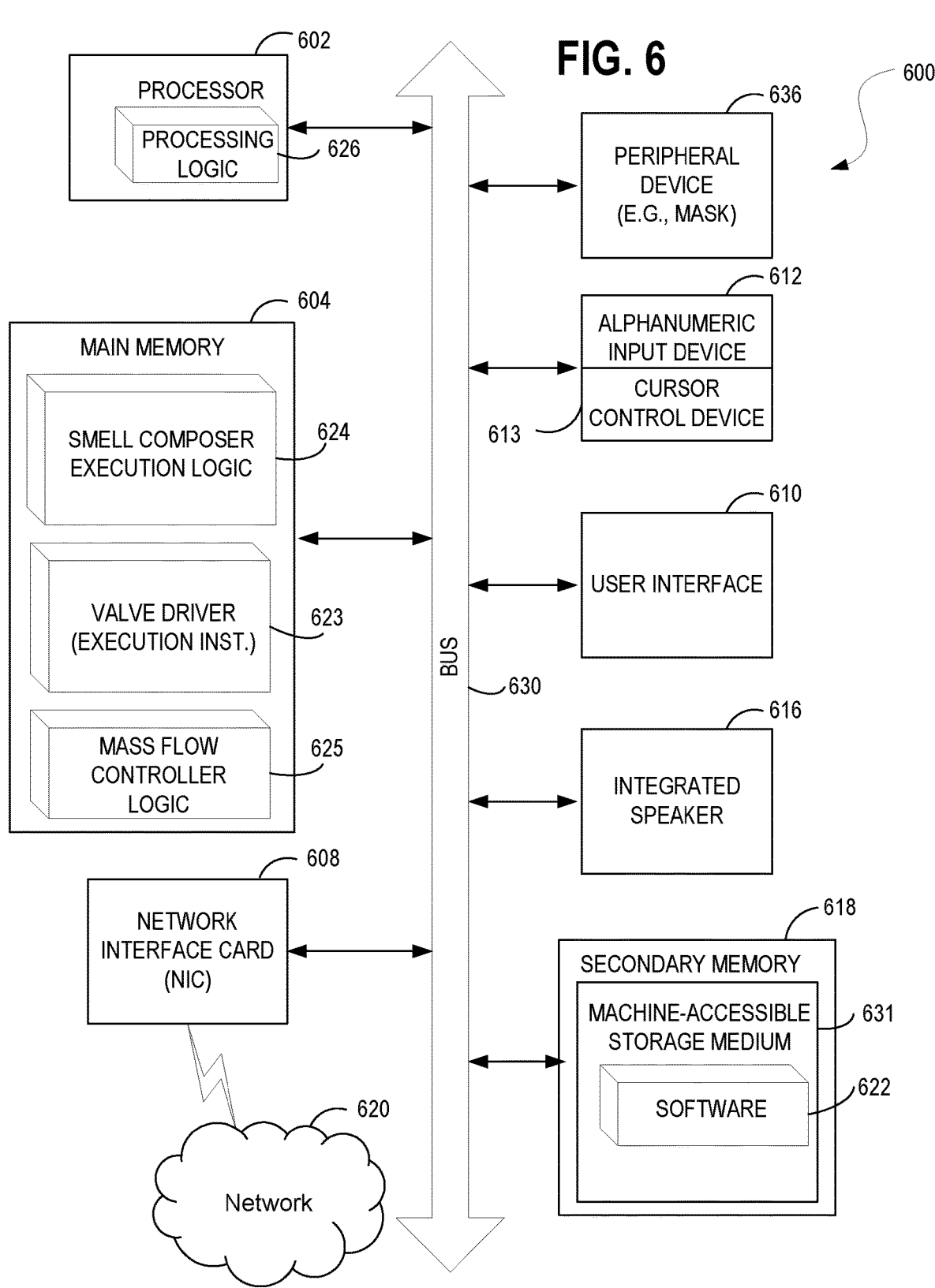
FIG. 6 illustrates a diagrammatic representation of a machine in the exemplary form of a computer system, in accordance with one embodiment.

FIG. 6 illustrates a diagrammatic representation of a machine 600 in the exemplary form of a computer system, in accordance with one embodiment, within which a set of instructions, for causing the machine/computer system 600 to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 600 includes a processor 602, a main memory 604 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 618 (e.g., a persistent storage device including hard disk drives and a persistent database and/or a multi-tenant database implementation), which communicate with each other via a bus 630. Main memory 604 includes a smell composer 624 for mixing desired odorant mixtures, including setting concentrations and interfacing with valve driver 622 to control valves across a manifold assembly, and controlling flow rates of gas-phase molecules via mass flow controller 623 and mass flow interface 635, in support of the methodologies and techniques described herein. Main memory 604 and its sub-elements are further operable in conjunction with processing logic 626 and processor 602 to perform the methodologies discussed herein.

Data acquisition API 634 may be associated with instruments such as NIDAQ instrument 304 to gather data from a virtual scene 301.

Processor 602 represents one or more specialized and specifically configured processing devices such as a microprocessor, central processing unit, or the like. More particularly, the processor 602 may be a complex instruction set computing (CISC) microprocessor, reduced instruction set computing (RISC) microprocessor, very long instruction word (VLAW) microprocessor, processor implementing other instruction sets, or processors implementing a combination of instruction sets. Processor 602 may also be one or more special-purpose processing devices such as an application-specific integrated circuit (ASIC), a field-programmable gate array (FPGA), a digital signal processor (DSP), network processor, or the like. Processor 602 is configured to execute the processing logic 626 for performing the operations and functionality discussed herein.

The computer system 601 may further include a network interface card 608. The computer system 601 also may include a user interface 610 (such as a video display unit, a liquid crystal display, etc.), an alphanumeric input device 612 (e.g., a keyboard), a cursor control device 613 (e.g., a mouse), and a signal generation device 616 (e.g., an integrated speaker). The computer system 601 may further include peripheral device 636 (e.g., wireless or wired communication devices, memory devices, storage devices, audio processing devices, video processing devices, etc.).

The secondary memory 618 may include a non-transitory machine-readable storage medium or a non-transitory computer readable storage medium or a non-transitory machine-accessible storage medium 631 on which is stored one or more sets of instructions (e.g., software 622) embodying any one or more of the methodologies or functions described herein. The software 622 may also reside, completely or at least partially, within the main memory 604 and/or within the processor 602 during execution thereof by the computer system 601, the main memory 604, and the processor 602 also constituting machine-readable storage media. The software 622 may further be transmitted or received over a network 620 via the network interface card 608.

According to a particular embodiment, there is an augmented reality olfactory delivery system having a set of one or more processors 602 and a main memory 604 communicably interfaced with odorant control hardware and operated by smell composer execution logic 624. According to such an embodiment, the augmented reality olfactory delivery system includes non-transitory instructions stored within either the memory or upon a non-transitory machine-readable storage medium that, when executed by the set of one or more processors, the instructions stored in the memory are configurable to cause the system to perform operations including: acquiring data from a virtual scene via a data acquisition API based on one or more of (i) positional information for an occupant, (ii) positional information for a virtual smell object, (iii) a desired odor index, and (iv) other environmental factors; determining an odor recipe for mixing one or more odorants via a smell composer executing at the olfactory delivery system; issuing instructions to an interfaced olfactometer to produce an odorant mixture by specifying a valve duty cycle and one or more odorants to be dispersed according to the odor recipe determined by the smell composer and an odor concentration; producing the odorant mixture at the interfaced olfactometer by instructing pneumatically connected valves across a manifold assembly to actuate in accordance with the valve duty cycle specified; pressurizing the odorant mixture to form gas-phase molecules; directing the gas-phase molecules into separate channels by setting flow rates via a mass flow controller; combining the gas-phase molecules of the separate channels into a combined flow for dispensing from a smell mask; and dispensing the gas-phase molecules into the smell mask, wherein the smell mask is configured to be affixed to a human user participating as an occupant within the virtual scene through which the gas-phase molecules are dispensed through the smell mask to represent to a human user olfactory sensations corresponding to the virtual smell object within the virtual scene.

FIG. 7 depicts flow diagrams illustrating a method for implementing olfactory delivery in virtualized environments using an olfactory delivery engine, in accordance with described embodiments.

Method 700 may be performed by processing logic that may include hardware (e.g., circuitry, dedicated logic, programmable logic, microcode, etc.), software (e.g., instructions run on a processing device to perform various operations such as interfacing functions, collecting, monitoring, diagnosing and reporting information, and executing/initiating instructions, or some combination thereof). In one embodiment, method 700 is performed or coordinated via system architecture such as that depicted at FIG. 5. Some of the blocks and/or operations listed below are optional in accordance with certain embodiments. The numbering of the blocks presented is for the sake of clarity and is not intended to prescribe an order of operations in which the various blocks must occur. Additionally, operations from method flow 1000 may be utilized in a variety of combinations.

Method 700 is performed by an augmented reality olfactory delivery engine having at least a processor and a memory therein which is specially configured to perform the following operations;

At block 705, processing logic acquires data from a virtual scene via a data acquisition API based on one or more of: (i) positional information for an occupant, (ii) positional information for a virtual smell object, (iii) a desired odor index, and (iv) other environmental factors.

At block 710, processing logic determines an odor recipe for mixing one or more odorants via a smell composer executing at the olfactory delivery system.

At block 715, processing logic issues instructions to an interfaced olfactometer to produce an odorant mixture by specifying a valve duty cycle and one or more odorants to be dispersed according to the odor recipe determined by the smell composer and an odor concentration.

At block 720, processing logic produces the odorant mixture at the interfaced olfactometer by instructing pneumatically connected valves across a manifold assembly to actuate in accordance with the valve duty cycle specified.

At block 725, processing logic pressurizes the odorant mixture to form gas-phase molecules and directs the gas-phase molecules into separate channels by setting flow rates via a mass flow controller.

At block 730, processing logic combines the gas-phase molecules of the separate channels into a combined flow for dispensing from a smell mask.

At block 735, processing logic dispenses the gas-phase molecules into the smell mask, in which the smell mask is configured to be affixed to a human user participating as an occupant within the virtual scene through which the gas-phase molecules are dispensed through the smell mask to represent to a human user olfactory sensations corresponding to the virtual smell object within the virtual scene.

According to another embodiment of method 700, dispensing the gas-phase molecules into the smell mask is custom configured to represent one or more virtual smell objects within the virtual scene to any human user wearing the smell mask through which the gas-phase molecules are dispensed.

According to another embodiment of method 700, the gas-phase molecules representing the one or more virtual smell objects within the virtual scene are calibrated temporally and spatially (through both time and virtual geographic space) to release to the human user when and where the virtual smell objects are encountered by the human user within the virtual scene.

According to another embodiment of method 700, each of the one or more odorants are associated with a single solenoid valve device pneumatically interfaced with and controlled by the olfactometer.

According to another embodiment of method 700, the augmented reality olfactory delivery engine integrates with spatial, visual, and auditory capabilities of virtual game engines.

According to another embodiment of method 700, one or more of: (i) the odor concentration, and (ii) the flow rate are dynamically adjustable in response to changes in the virtual scene via a virtual scene interface to the smell engine.

According to another embodiment of method 700, changes in the virtual scene include changes in the position of the human user as an occupant within the virtual scene.

According to another embodiment of method 700, the dispensed gas-phase molecules represent the virtual smell object are captured via odor recording technologies and rendered using olfactory display technologies.

According to another embodiment of method 700, the augmented reality olfactory delivery engine is used in the context of at least one of (i) medical evaluation and diagnosis, (ii) medical rehabilitation and therapy, (iii) medical research, (iv) educational programs, (v) gaming activity, (vi) simulation of extreme environments, (vii) simulation of outer space, (viii) developing products and services, (ix) aromatherapy, (x) cosmetic fragrances, (xi) rest and relaxation services, and (xii) the food industry.

According to another embodiment of method 700, the augmented reality olfactory delivery engine is used for application of medical rehabilitation including treatment of a medical condition selected from the group including: (i) stroke. (ii) mental health conditions, (iii) cardiovascular disease, (iv) neurodegenerative disease, (v) neurological injury, and (vi) traumatic brain injury.

According to another embodiment of method 700, the augmented reality olfactory delivery engine is used in simulation of extreme environments selected from the group including: (i) battlefield, (ii) disaster zone, (iii) geographically remote location, (iv) extreme-climate environment, and (v) extraterrestrial environment.

According to another embodiment of method 700, the augmented reality olfactory delivery engine assists with memory and recall via pairing the simulating of desired olfactory sensation within the senses of the wearer of the smell mask and one or more of (i) presentation of desired information, (ii) actions within the virtual scene, and (iii) objects within the virtual scene.

For example, when an astronaut trains in a virtual environment using the olfactory delivery engine, dispensing a specific pleasant odor after the astronaut correctly performs a spacecraft navigation or control procedure may serve as positive reinforcement to assist the astronaut with memory and recall of the procedure, much like the famous Pavlov's Dog experiment. Likewise, negative reinforcement may also be used in virtual environments using the olfactory delivery engine. According to certain embodiments, this may be accomplished via the olfactory delivery engine dispensing unpleasant odors when a user-occupant in virtual environments performs undesirable or incorrect actions such as incorrect navigation, or to warn the user-occupant to avoid dangerous virtual objects such as wild animals or natural hazards.

According to another embodiment of method 700, the augmented reality olfactory delivery engine improves olfactory capabilities of the human user when wearing the smell mask via one or more of (i) eye-tracking for smell identification, and (ii) training the wearer to identify odors via repeated smell-masking procedures.

For example, using the olfactory delivery engine, a user-occupant of a virtual environment may be trained to recognize various odors and objects associated with those odors such as the scents of various plant varieties based on odor alone, without visual, auditory, haptic, or gustatory stimulation.

According to another embodiment of method 700, constant flow is maintained during one or more of: (i) pressurizing the desired odorant mixture to gas-phase molecules, and (ii) dispensing the gas-phase molecules.

According to another embodiment of method 700, an optimization module improves one or more of: (i) matching odor recipes to desired odors via manipulating combinations and concentrations of odorants, (ii) determining best airflow rates and valve duty cycles to pressurize liquid odorants to gas-phase molecules, (iii) determining components that can be ignored or clipped to meet human sensory needs, (iv) specifying varied odor strengths for artificial synthesis. (v) integrating software in real-time with 3D game engines, (vi) providing a programmable environment for developers to specify virtual odor position(s) in virtual environments/spaces, (vii) adapting odor composition according to virtual distance-based on-the-fly dynamics, and (viii) making optimization decision regarding which odorants are capable of making mixtures at different ratios and concentrations.

According to a particular embodiment, there is a non-transitory computer readable storage medium having instructions stored thereupon that, when executed by an augmented reality olfactory delivery system having at least a processor and a memory communicably interfaced with odorant control hardware, the instructions cause the augmented reality olfactory delivery system to perform operations including: acquiring data from a virtual scene via a data acquisition API based on one or more of (i) positional information for an occupant, (ii) positional information for a virtual smell object, (iii) a desired odor index, and (iv) other environmental factors; determining an odor recipe for mixing one or more odorants via a smell composer executing at the olfactory delivery system; issuing instructions to an interfaced olfactometer to produce an odorant mixture by specifying a valve duty cycle and one or more odorants to be dispersed according to the odor recipe determined by the smell composer and an odor concentration: producing the odorant mixture at the interfaced olfactometer by instructing pneumatically connected valves across a manifold assembly to actuate in accordance with the valve duty cycle specified; pressurizing the odorant mixture to form gas-phase molecules; directing the gas-phase molecules into separate channels by setting flow rates via a mass flow controller; combining the gas-phase molecules of the separate channels into a combined flow for dispensing from a smell mask; and dispensing the gas-phase molecules into the smell mask, wherein the smell mask is configured to be affixed to a human user participating as an occupant within the virtual scene through which the gas-phase molecules are dispensed through the smell mask to represent to a human user olfactory sensations corresponding to the virtual smell object within the virtual scene.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system to execute at an augmented reality olfactory delivery engine to simulate odors, wherein the system comprises:

a memory to store instructions;

a set of one or more processors;

a non-transitory machine-readable storage medium that provides instructions that, when executed by the set of one or more processors, the instructions stored in the memory are configurable to cause the system to perform operations comprising:

acquiring data from a virtual scene via a data acquisition API based on one or more of:

(i) positional information for an occupant, (ii) positional information for a virtual smell object, (iii) a desired odor index, and (iv) other environmental factors;

determining an odor recipe for mixing one or more odorants via a smell composer executing at the augmented reality olfactory delivery engine, wherein determining the odor recipe further includes continuously updating one or more hardware control parameters of an interfaced olfactometer, including at least valve duty cycles and mass flow controller setpoints, based on changes in relative spatial distance between the occupant and the virtual smell object;

issuing instructions to the interfaced olfactometer to produce an odorant mixture by specifying a valve duty cycle and one or more odorants to be dispersed according to the odor recipe determined by the smell composer and an odor concentration;

producing the odorant mixture at the interfaced olfactometer by instructing pneumatically-connected valves across a manifold assembly to actuate in accordance with the valve duty cycle specified;

pressurizing the odorant mixture to form gas-phase molecules:

directing the gas-phase molecules into separate channels by setting flow rates via a mass flow controller;

combining the gas-phase molecules of the separate channels into a combined flow for dispensing from a smell mask; and dispensing the gas-phase molecules into the smell mask, wherein the smell mask is configured to be affixed to a human user participating as an occupant within the virtual scene through which the gas-phase molecules are dispensed through the smell mask to represent to a human user olfactory sensations corresponding to the virtual smell object within the virtual scene.

2. The system of claim 1, wherein the one or more odorants are each associated with a single solenoid valve device.

3. The system of claim 1, wherein the augmented reality olfactory delivery engine integrates with spatial, visual, and auditory capabilities of virtual game engines.

4. The system of claim 1, wherein one or more of:

(i) a desired odor concentration, and (ii) a desired flow rate are dynamically adjustable in response to changes in the virtual scene via a virtual interface, wherein changes in the virtual scene include changes in the position of the occupant of the virtual scene relative to the virtual smell object.

5. The system of claim 1, wherein dispensed gas-phase molecules represent the virtual smell object are captured via odor recording technologies and rendered using olfactory display technologies.

6. The system of claim 1, wherein the augmented reality olfactory delivery engine is used in a context of:

(i) medical evaluation and diagnosis, (ii) medical rehabilitation and therapy, (iii) medical research, (iv) educational programs, (v) gaming activity, (vi) simulation of extreme environments, (vii) simulation of outer space, (viii) developing products and services, (ix) aromatherapy, (x) cosmetic fragrances, (xi) rest and relaxation services, and (xii) a food industry.

7. The system of claim 6, wherein the augmented reality olfactory delivery engine is used in a context of medical rehabilitation of:

(i) stroke, (ii) mental health conditions, (iii) cardiovascular disease, (iv) neurodegenerative disease, (v) neurological injury, and (vi) traumatic brain injury.

8. The system of claim 6, wherein the augmented reality olfactory delivery engine is used in simulation of extreme environments, wherein extreme environments includes one or more of a:

(i) battlefield, (ii) disaster zone, (iii) geographically remote location, (iv) extreme-climate environment, and (v) extraterrestrial environment.

9. The system of claim 1, wherein the augmented reality olfactory delivery engine assists with memory and recall via pairing the simulating of desired olfactory sensation within the senses of a wearer of the smell mask and one or more of:

(i) presentation of desired information, (ii) actions within the virtual scene, and (iii) objects within the virtual scene.

10. The system of claim 1, wherein the augmented reality olfactory delivery engine improves wearer olfactory capabilities via one or more of:

(i) eye-tracking for smell identification, and (ii) training a wearer to identify odors via repeated smell-masking procedures.

11. The system of claim 1, wherein a constant flow is maintained across the manifold assembly during one or more of:

(i) pressurizing a desired odorant mixture to gas-phase molecules, and (ii) dispensing the gas-phase molecules.

12. The system of claim 1, wherein the operations further comprise utilizing an optimization module to improve one or more of:

(i) matching odor recipes to desired odors via manipulating combinations and concentrations of odorants, (ii) determining airflow rates and the valve duty cycles to pressurize liquid odorants to gas-phase molecules, (iii) determining components that can be ignored or clipped to meet human sensory needs, (iv) specifying varied odor strengths for artificial synthesis, (v) integrating software in real-time with 3D game engines, (vi) providing a programmable environment for developers to specify virtual odor position(s) in virtual environments/spaces, (vii) adapting odor composition according to virtual distance-based on-the-fly dynamics, and (viii) making optimization decisions regarding which odorants are capable of making mixtures at different ratios and concentrations.

13. A method performed by an augmented reality olfactory delivery system having at least a processor and a memory communicably interfaced with odorant control hardware, the method comprising:

acquiring data from a virtual scene via a data acquisition API based on one or more of:

(i) positional information for an occupant, (ii) positional information for a virtual smell object, (iii) a desired odor index, and (iv) other environmental factors;

determining an odor recipe for mixing one or more odorants via a smell composer executing at the augmented reality olfactory delivery system, wherein determining the odor recipe further includes continuously updating one or more hardware control parameters of an interfaced olfactometer, including at least valve duty cycles and mass flow controller setpoints, based on changes in relative spatial distance between the occupant and the virtual smell object; issuing instructions to the interfaced olfactometer to produce an odorant mixture by specifying a valve duty cycle and one or more odorants to be dispersed according to the odor recipe determined by the smell composer and an odor concentration;

producing the odorant mixture at the interfaced olfactometer by instructing pneumatically-connected valves across a manifold assembly to actuate in accordance with the valve duty cycle specified;

pressurizing the odorant mixture to form gas-phase molecules;

directing the gas-phase molecules into separate channels by setting flow rates via a mass flow controller;

combining the gas-phase molecules of the separate channels into a combined flow for dispensing from a smell mask; and dispensing the gas-phase molecules into the smell mask, wherein the smell mask is configured to be affixed to a human user participating as an occupant within the virtual scene through which the gas-phase molecules are dispensed through the smell mask to represent to a human user olfactory sensations corresponding to the virtual smell object within the virtual scene.

14. The method of claim 13:

wherein dispensing the gas-phase molecules into the smell mask is custom configured to represent one or more virtual smell objects within the virtual scene to any human user wearing the smell mask through which the gas-phase molecules are dispensed; and wherein the gas-phase molecules representing the one or more virtual smell objects within the virtual scene are calibrated temporally and spatially to release to the human user when and where the virtual smell objects are encountered by the human user within the virtual scene based on the relative spatial distance.

15. The method of claim 13, wherein each of the one or more odorants are associated with a single solenoid valve device pneumatically interfaced with and controlled by the olfactometer.

16. The method of claim 13, wherein the augmented reality olfactory delivery system integrates with spatial, visual, and auditory capabilities of virtual game engines.

17. The method of claim 13:

wherein one or more of:

(i) the odor concentration, and (ii) the flow rate are dynamically adjustable in response to changes in the virtual scene via a virtual scene interface to a smell engine; and wherein changes in the virtual scene include changes in the position of the human user as an occupant within the virtual scene relative to the virtual smell object.

18. The method of claim 13, wherein dispensed gas-phase molecules represent the virtual smell object are captured via odor recording technologies and rendered using olfactory display technologies.

19. The method of claim 13, wherein the augmented reality olfactory delivery system is used in a context of at least one of:

(i) medical evaluation and diagnosis, (ii) medical rehabilitation and therapy, (iii) medical research, (iv) educational programs, (v) gaming activity, (vi) simulation of extreme environments, (vii) simulation of outer space, (viii) developing products and services, (ix) aromatherapy, (x) cosmetic fragrances, (xi) rest and relaxation services, and (xii) a food industry.

20. Non-transitory computer readable storage media having instructions stored thereupon that, when executed by system having at least a processor and a memory therein, the instructions cause the processor to implement an augmented reality olfactory delivery engine configurable to perform the following operations:

acquiring data from a virtual scene via a data acquisition API based on one or more of:

(i) positional information for an occupant, (ii) positional information for a virtual smell object, (iii) a desired odor index, and (iv) other environmental factors;

determining an odor recipe for mixing one or more odorants via a smell composer executing at the augmented reality olfactory delivery engine, wherein determining the odor recipe further includes continuously updating one or more hardware control parameters of the interfaced olfactometer, including at least valve duty cycles and mass flow controller setpoints, based on changes in relative spatial distance between the occupant and the virtual smell object;

issuing instructions to an interfaced olfactometer to produce an odorant mixture by specifying a valve duty cycle and one or more odorants to be dispersed according to the odor recipe determined by the smell composer and an odor concentration;

producing the odorant mixture at the interfaced olfactometer by instructing pneumatically-connected valves across a manifold assembly to actuate in accordance with the valve duty cycle specified;

pressurizing the odorant mixture to form gas-phase molecules;

directing the gas-phase molecules into separate channels by setting flow rates via a mass flow controller;

combining the gas-phase molecules of the separate channels into a combined flow for dispensing from a smell mask; and dispensing the gas-phase molecules into the smell mask, wherein the smell mask is configured to be affixed to a human user participating as an occupant within the virtual scene through which the gas-phase molecules are dispensed through the smell mask to represent to a human user olfactory sensations corresponding to the virtual smell object within the virtual scene.

\* \* \* \* \*